(12) United States Patent
Zhang et al.

(10) Patent No.: US 11,192,850 B2
(45) Date of Patent: Dec. 7, 2021

(54) N-ARYL OXAMIC ACIDS

(71) Applicant: Purdue Research Foundation, West Lafayette, IN (US)

(72) Inventors: Zhong-Yin Zhang, West Lafayette, IN (US); Kasi Viswanatharaju Ruddraraju, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/163,650

(22) Filed: Feb. 1, 2021

(65) Prior Publication Data

US 2021/0309606 A1    Oct. 7, 2021

Related U.S. Application Data

(60) Provisional application No. 63/005,485, filed on Apr. 6, 2020.

(51) Int. Cl.
| | | |
|---|---|---|
| *C07C 235/74* | (2006.01) |
| *A61P 31/06* | (2006.01) |
| *C07C 317/14* | (2006.01) |
| *C07D 215/48* | (2006.01) |

(52) U.S. Cl.
CPC ............ *C07C 235/74* (2013.01); *A61P 31/06* (2018.01); *C07C 317/14* (2013.01); *C07D 215/48* (2013.01)

(58) Field of Classification Search
CPC ... C07C 235/74; C07C 317/14; C07D 215/48; A61P 31/06
See application file for complete search history.

(56) References Cited

U.S. PATENT DOCUMENTS

2008/0207722 A1\*  8/2008  Bombrun ................ A61P 37/00
                                                                    514/404

\* cited by examiner

*Primary Examiner* — Timothy R Rozof
(74) *Attorney, Agent, or Firm* — Purdue Research Foundation

(57) ABSTRACT

The present disclosure relates to novel N-aryl oxamic acid based inhibitors for *Mycobacterium tuberculosis* protein tyrosine phosphatase B (mPTPB), and to the method of making and using the novel N-aryl oxamic acid based inhibitors. More specifically, compounds provided in this disclosure can be used to inhibit *Mycobacterium tuberculosis* protein tyrosine phosphatase B (mPTPB) and to treat a patient having a Tuberculosis disease.

8 Claims, No Drawings

N-ARYL OXAMIC ACIDS

GOVERNMENT RIGHTS

This invention was made with government support under Award No. RO1 CA207288 awarded by the National Institutes of Health (NIH). The government has certain rights in the invention.

TECHNICAL FIELD

The present disclosure relates to novel N-aryl oxamic acid based inhibitors for *Mycobacterium tuberculosis* protein tyrosine phosphatase B (mPTPB), and to the method of making and using the novel N-aryl oxamic acid based inhibitors.

BACKGROUND

This section introduces aspects that may help facilitate a better understanding of the disclosure. Accordingly, these statements are to be read in this light and are not to be understood as admissions about what is or is not prior art.

Protein tyrosine phosphatases (PTPs) counterbalance the activity of protein tyrosine kinases (PTKs), and consequently, these two enzyme families have a central role in determining the status of protein tyrosine phosphorylation inside the cell. The phosphorylation of a protein can alter its enzymatic activity, subcellular localization, macromolecular interactions, stability, and ultimately control normal cellular homeostasis and disease processes. Dysregulation of PTPs is associated with a multitude of diseases, and many members of the PTP family have been recognized as potential therapeutic targets. Potent and selective inhibitors of PTPs are essential for interrogating the biological function of the PTPs, and they may ultimately be developed into valuable therapeutics in the treatment of several pathological human conditions, including cancer, autoimmune disorders and infectious diseases.

Tuberculosis (TB), an infectious disease caused by the bacteria called *Mycobacterium tuberculosis* (Mtb), is one of the top 10 causes of human death worldwide. In 2017, an estimated 10 million people became ill with TB, and 1.6 million people died of TB (including 0.3 million people with HIV associated TB). It is also estimated that about one-quarter of the world's population has latent TB (people have been infected by TB but are not ill (yet) with the disease). The major obstacle in the treatment of TB is antibiotic resistance; due to the lack of compliance from patients during a lengthy and complex course of treatment. The rapid emergence of multidrug-resistant (MDR) and extensively drug-resistant (XDR) TB demands the development of new therapeutic agents with novel molecular targets and mechanisms of actions. Antivirulence strategies are now emerging as an alternative therapeutic approach to combat antibiotic resistance in a number of microbial infections including TB. *Mycobacterium tuberculosis* protein tyrosine phosphatase B (mPTPB) is a virulence factor that is secreted into the host macrophages. mPTPB is critical for the survival of Mtb and persistence of the infection inside the macrophages of animal models. Deletion of mPTPB has no effect on the growth of the pathogen itself but reduces the intracellular survival of Mtb in infected macrophages and reduces the bacterial load in a guinea pig model of TB infection. Once inside the host cells, mPTPB subverts the innate immune responses by blocking the ERK1/2 and p38 kinase mediated cytokine production and promoting cell survival through the Akt pathway. Inhibition of mPTPB with small molecule inhibitors can reverse the altered host immune responses induced by the bacterial phosphatase and impairs the survival of MDR-TB in human macrophages and reduces infection burden in guinea pig models. Selective inhibition of mPTPB also increases the intracellular killing efficacy of first-line antibiotics rifampicin and isoniazid, indicating their suitability for combination therapies. These results provide important proof-of-concept for the notion that specific inhibitors of mPTPB may serve as effective anti-TB agents. Targeting the virulent mPTPB is expected to specifically undermine pathogen-host interactions without adverse effects on bacterial growth, therefore exerting less selective pressure for drug resistance. More importantly, the lack of a human orthologue (minimal side effects on the host) makes mPTPB an attractive drug target for specific treatment of TB. Moreover, mPTPB inhibitors function within the host macrophage cytosol and mechanistically do not overlap with existing anti-TB agents; they may compliment/synergize with lengthy standard TB treatment of six to nine months. Lastly, since mPTPB acts outside of the bacterium, mPTPB inhibitors are not required to cross the thick, hydrophobic, and waxy mycobacterial cell wall, which presents a significant challenge for the efficient delivery of traditional antibacterial agents.

The design and synthesis of inhibitors for PTPs with optimal potency, selectivity, and pharmacological properties remain a challenging endeavor, mostly due to the highly conserved and positively charged nature of PTP active sites.

SUMMARY

The present disclosure relates to novel N-aryl oxamic acid based inhibitors for *Mycobacterium tuberculosis* protein tyrosine phosphatase B (mPTPB), and to the method of making and using the novel N-aryl oxamic acid based inhibitors.

In one embodiment, the present disclosure provides a compound of formula I:

or a stereoisomer, tautomer, solvate, pharmaceutically acceptable salt thereof, wherein:

$(R^1)_n$ represents 1-3 independent $R^1$ being attached to the phenyl ring, wherein n is 1-3, wherein each of said 1-3 $R^1$ independently represents a H, F, Cl, Br, I, —CN, —$OR^2$, —$COOR^3$, —$NR^4R^5$, —CO—$R^6$, —$SO_2NR^7R8$, an optionally substituted $C_1$-$C_8$ branched or unbranched alkyl chain, an optionally substituted $C_3$-$C_8$ cyclic alkyl, an optionally substituted aryl. or an optionally substituted heteroaryl comprising one or more O, N, or S, or when n is 2, two independent $R^1$ can join together to form a fused bicyclic ring with the phenyl ring; and $R^2$-$R^8$ each independently represents a H, an optionally substituted $C_1$-$C_8$ branched or unbranched alkyl chain, an optionally substituted $C_3$-$C_8$ cyclic alkyl, an optionally substituted aryl, or an optionally substituted heteroaryl comprising one or more O, N, or S, or a nitrogen protecting group.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A "hetero aryl" represents aromatic ring comprising at least one hetero atom such as N, S, O, or Se. Hetero aryl in the present disclosure may be any hetero aryl. Hetero aryl in the present disclosure may be but is not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, benzimidazolinyl groups, or any combination thereof.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The design and synthesis of inhibitors for PTPs with optimal potency, selectivity, and pharmacological properties remain a challenging endeavor, mostly due to the highly conserved and positively charged nature of PTP active sites. To enable the engagement with the positively charged active site pockets, numerous negatively charged functional group-containing compounds such as carboxylic acids, salicylic acids, sulfamic acids, α-sulfophenylacetic amide (SPAA), and 2-oxalylaminobenzoic acid (OBA) have been reported as nonhydrolyzable phosphotyrosine (pTyr) mimetics for the inhibition of various members of the PTP family. OBA was reported as a competitive, reversible inhibitor of protein-tyrosine phosphatase 1B (PTP1B) and co-crystal structures of this chemical class were also described (Scheme 1). OBA was further optimized by structure-based design to generate several highly potent PTP1B inhibitors, such as compounds II, III, and IV (Scheme 1). Though potent ($K_i$ values in the nM range), the high polar surface area (PSA), molecular mass, and charge of these compounds make further optimization difficult. Compound V was identified as a PTP1B inhibitor using high throughput X-ray crystallography technique. This compound showed an $IC_{50}$ of 86 □M against PTP1B, and no selectivity studies or further modifications of V were reported by the authors. Compound (oxalylamino methylene)-thiophene sulfonamide (OMTS, VI) was reported as a competitive inhibitor for mPTPB. Compound VI showed an $IC_{50}$ of 440 t 50 nM and over 60-fold selectivity for mPTPB over six human PTPs, although no cellular activity data was provided for VI.

Scheme 1: Previously reported oxamic acids based pTyr mimetrics for PTP inhibition

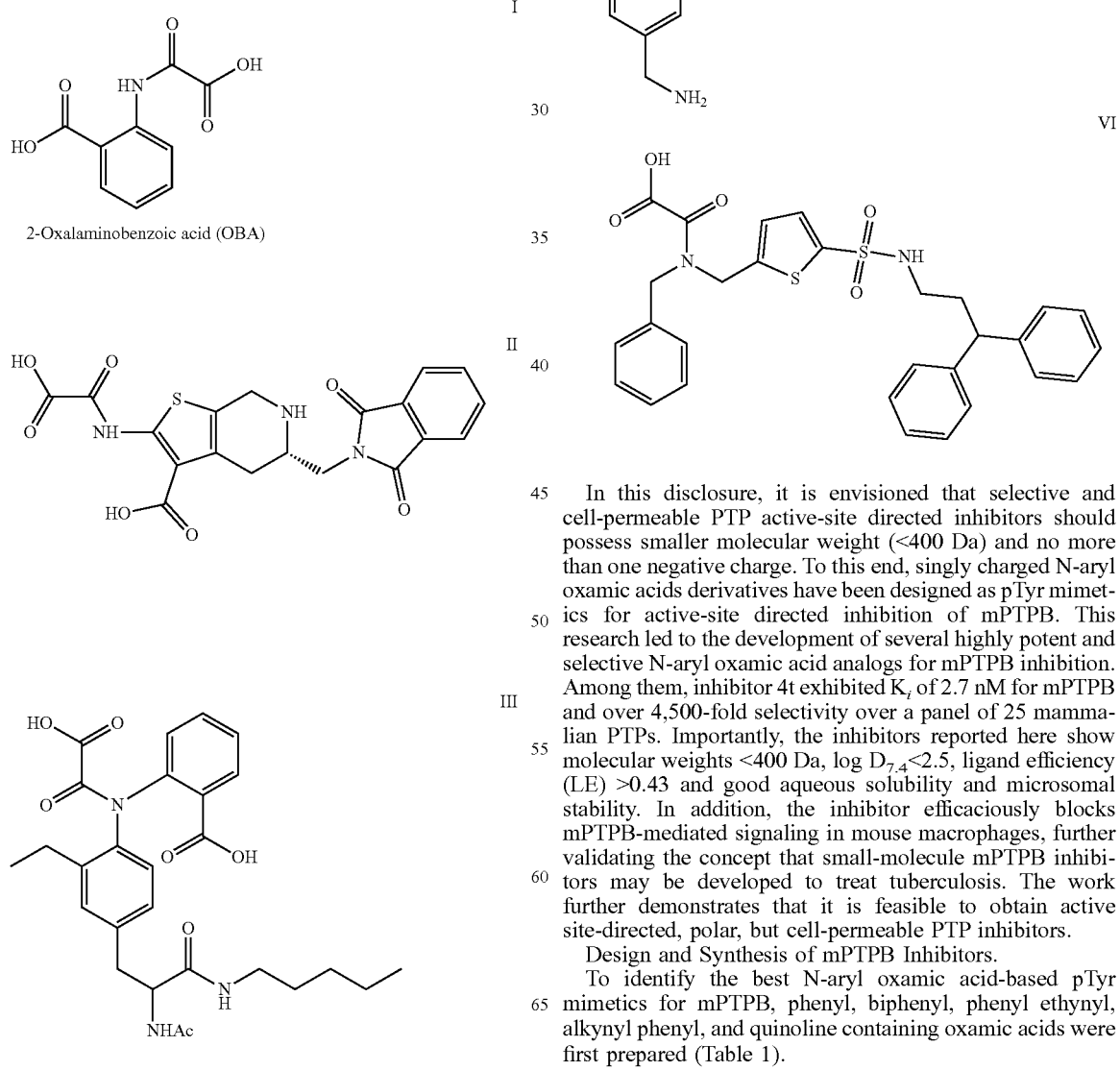

In this disclosure, it is envisioned that selective and cell-permeable PTP active-site directed inhibitors should possess smaller molecular weight (<400 Da) and no more than one negative charge. To this end, singly charged N-aryl oxamic acids derivatives have been designed as pTyr mimetics for active-site directed inhibition of mPTPB. This research led to the development of several highly potent and selective N-aryl oxamic acid analogs for mPTPB inhibition. Among them, inhibitor 4t exhibited $K_i$ of 2.7 nM for mPTPB and over 4,500-fold selectivity over a panel of 25 mammalian PTPs. Importantly, the inhibitors reported here show molecular weights <400 Da, log $D_{7.4}$<2.5, ligand efficiency (LE) >0.43 and good aqueous solubility and microsomal stability. In addition, the inhibitor efficaciously blocks mPTPB-mediated signaling in mouse macrophages, further validating the concept that small-molecule mPTPB inhibitors may be developed to treat tuberculosis. The work further demonstrates that it is feasible to obtain active site-directed, polar, but cell-permeable PTP inhibitors.

Design and Synthesis of mPTPB Inhibitors.

To identify the best N-aryl oxamic acid-based pTyr mimetics for mPTPB, phenyl, biphenyl, phenyl ethynyl, alkynyl phenyl, and quinoline containing oxamic acids were first prepared (Table 1).

TABLE 1

IC$_{50}$ values of various oxamic acid derivatives against mPTPB, PTP1B and SHP2

| | 1 | 2 | 3 | 4 |
|---|---|---|---|---|
| mPTPB IC$_{50}$ (μM) = | 5.4 ± 1.4 | 4.3 ± 1.0 | 1.5 ± 0.2 | 0.257 ± 0.008 |
| PTP1B IC$_{50}$ (μM) = | >100 | >100 | >100 | >100 |
| SHP2 IC$_{50}$ (μM) = | >100 | >100 | 58 ± 2 | >100 |

| | 5 | 6 | 7 | 8 |
|---|---|---|---|---|
| mPTPB IC$_{50}$ (μM) = | 0.562 ± 0.019 | 0.666 ± 0.025 | 8.4 ± 0.2 | >10 |
| PTP1B IC$_{50}$ (μM) = | >100 | 62 ± 5 | >100 | >100 |
| SHP2 IC$_{50}$ (μM) = | 69 ± 4 | 29 ± 8 | >100 | >100 |

Compounds 1 to 8 were prepared by a reaction between the corresponding aryl amine and methyl chlorooxoacetate in a N,N-diisopropyl ethylamine/tetrahydrofuran reaction followed by mild hydrolysis using 1N KOH/THF (1:1 v/v) solution. The effort to synthesize other bicyclic (naphthyl, benzoxazole, and benzothiazole) based oxamic acids resulted in compounds with poor solubility profiles, likely due to a higher degree of molecular planarity. Half-inhibitory concentration values (IC$_{50}$) of 1 to 8 were measured in a p-nitrophenyl phosphate (pNPP) assay against mPTPB, PTP1B and SHP2 phosphatases. Among the compounds shown in Table 1, the phenyl ethynyl containing analogs (4 and 5) demonstrated superior inhibition and selectivity for mPTPB in comparison to the biphenyl, alkyl, or bicyclic analogs (2, 3, 6, 7, and 8). Importantly, para derivative 4 showed 2-fold more potency compared to the meta derivative 5, and a similar trend was observed in the case of compounds 6 and 7. These results suggest the preference for para substitution over meta for mPTPB inhibition. Consequently, several analogs of compound 4 were prepared to further improve its activity against mPTPB. Depending on the commercial availability of the starting materials (aryl halides and aryl alkynes), two different synthetic strategies were used to prepare analogs of 4. In the first strategy, 4-ethynyl or 3-ethynyl aniline was treated with methyl chlorooxoacetate in a N,N-diisopropyl ethylamine/tetrahydrofuran reaction to yield the corresponding oxamate ester. Subsequently, the oxamate ester was treated with various aryl halides in a Sonogashira coupling reaction using Pd(PPh₃)Cl₂, CuI, Na₂CO₃, and dimethylformamide (DMF) to provide phenylethynyl oxamate esters in good yields. A mild hydrolysis of these esters using 1N KOH/THF furnished the final compounds in excellent yields (Scheme 2A). In the second strategy, 4-iodoaniline was treated with methyl chlorooxoacetate in a N,N-diisopropyl ethylamine/tetrahydrofuran reaction to yield methyl 2-((4-iodophenyl)amino)-2-oxoacetate (Scheme 1B). Sonogashira coupling reaction of the ester with alkynes followed by mild hydrolysis provided final compounds in excellent yields.

Scheme 2. Strategies for the synthesis of mPTPB inhibitors. A) Synthesis of phenylethynyl oxamic acids from ethynylanilines. B) Synthesis of phenylethynyl oxamic acids from 4-iodoaniline

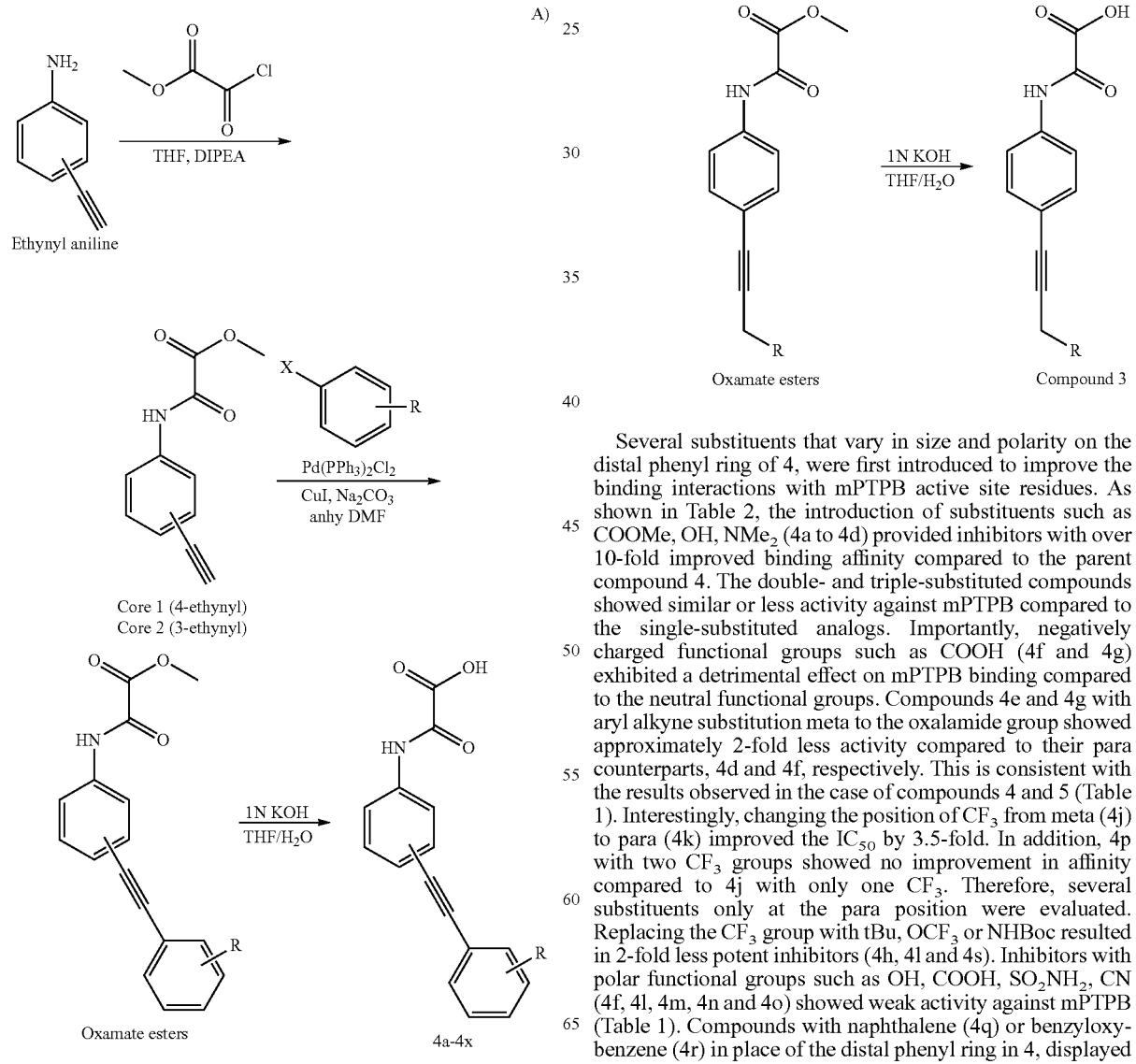

Several substituents that vary in size and polarity on the distal phenyl ring of 4, were first introduced to improve the binding interactions with mPTPB active site residues. As shown in Table 2, the introduction of substituents such as COOMe, OH, NMe₂ (4a to 4d) provided inhibitors with over 10-fold improved binding affinity compared to the parent compound 4. The double- and triple-substituted compounds showed similar or less activity against mPTPB compared to the single-substituted analogs. Importantly, negatively charged functional groups such as COOH (4f and 4g) exhibited a detrimental effect on mPTPB binding compared to the neutral functional groups. Compounds 4e and 4g with aryl alkyne substitution meta to the oxalamide group showed approximately 2-fold less activity compared to their para counterparts, 4d and 4f, respectively. This is consistent with the results observed in the case of compounds 4 and 5 (Table 1). Interestingly, changing the position of CF₃ from meta (4j) to para (4k) improved the IC₅₀ by 3.5-fold. In addition, 4p with two CF₃ groups showed no improvement in affinity compared to 4j with only one CF₃. Therefore, several substituents only at the para position were evaluated. Replacing the CF₃ group with tBu, OCF₃ or NHBoc resulted in 2-fold less potent inhibitors (4h, 4l and 4s). Inhibitors with polar functional groups such as OH, COOH, SO₂NH₂, CN (4f, 4l, 4m, 4n and 4o) showed weak activity against mPTPB (Table 1). Compounds with naphthalene (4q) or benzyloxybenzene (4r) in place of the distal phenyl ring in 4, displayed poor solubility and selectivity (Table 2).

TABLE 2

IC$_{50}$ values fo compound 4, 4a-4s against a panel of PTPs

| Entry | Structure | mPTPB IC$_{50}$ (μM) | SHP2 IC$_{50}$ (μM) | SHP1 IC$_{50}$ (μM) | PTP1B IC$_{50}$ (μM) |
|---|---|---|---|---|---|
| 4 | 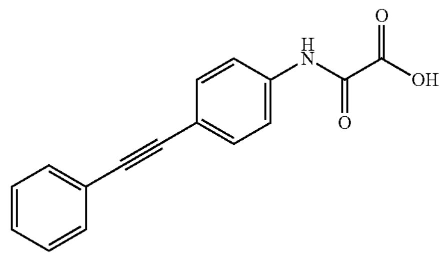 [SMILES: O=C(O)C(=O)Nc1ccc(C#Cc2ccccc2)cc1] | 0.257 ± 0.008 | >100 | >100 | >100 |
| 4a | 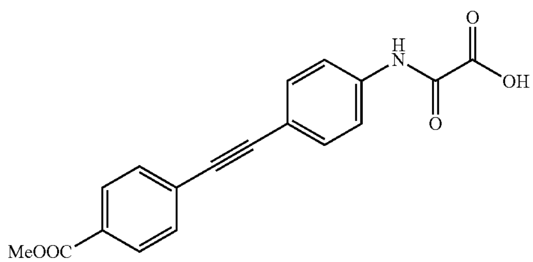 [SMILES: COC(=O)c1ccc(C#Cc2ccc(NC(=O)C(=O)O)cc2)cc1] | 0.023 ± 0.004 | 52.6 ± 6.4 | >100 | >100 |
| 4b | 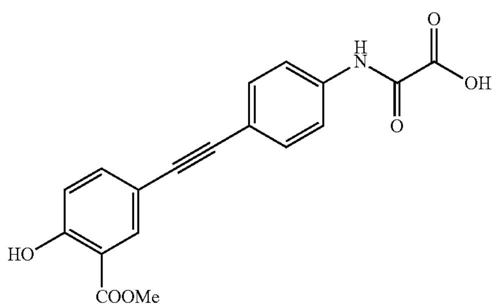 [SMILES: COC(=O)c1cc(C#Cc2ccc(NC(=O)C(=O)O)cc2)ccc1O] | 0.025 ± 0.003 | 27.3 ± 3.3 | >50 | >50 |
| 4c | 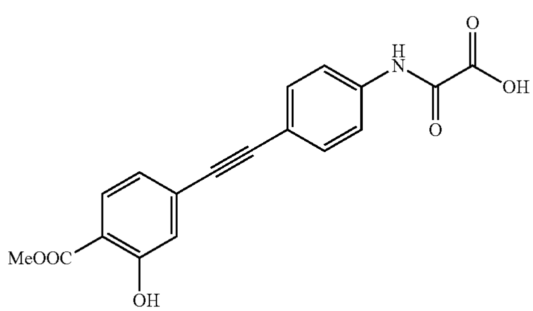 [SMILES: COC(=O)c1ccc(C#Cc2ccc(NC(=O)C(=O)O)cc2)cc1O] | 0.032 ± 0.006 | >50 | >50 | >50 |
| 4d | 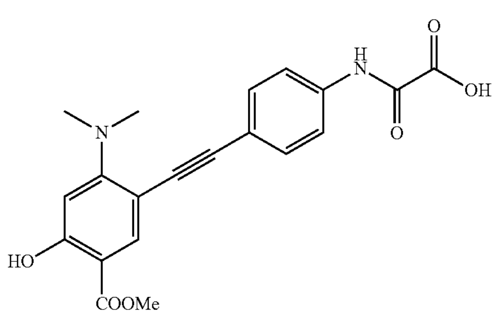 [SMILES: CN(C)c1cc(O)c(C(=O)O)cc1C#Cc1ccc(NC(=O)C(=O)O)cc1] | 0.030 ± 0.009 | >50 | >50 | >50 |

TABLE 2-continued
IC$_{50}$ values fo compound 4, 4a-4s against a panel of PTPs
| Entry | Structure | mPTPB IC$_{50}$ (μM) | SHP2 IC$_{50}$ (μM) | SHP1 IC$_{50}$ (μM) | PTP1B IC$_{50}$ (μM) |
|---|---|---|---|---|---|
| 4e | 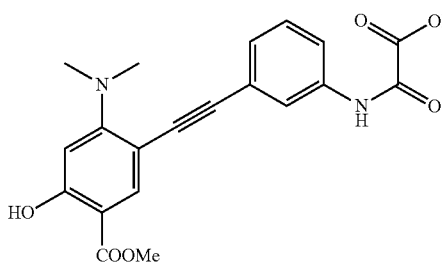 | 0.057 ± 0.012 | >50 | >50 | >50 |
| 4f | 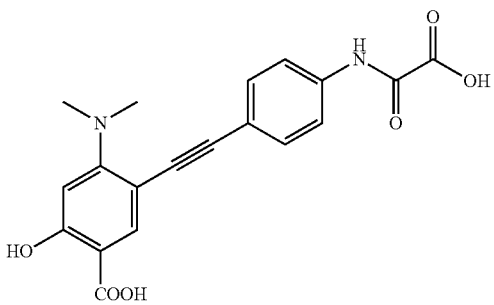 | 0.090 ± 0.008 | 78.5 ± 4.2 | 59.3 ± 6.0 | >100 |
| 4g | 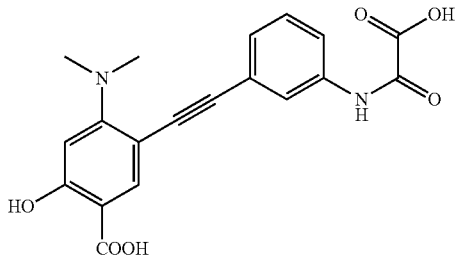 [SMILES: CN(C)c1cc(O)c(C(=O)O)cc1C#Cc1cccc(NC(=O)C(=O)O)c1] | 0.160 ± 0.015 | 47.5 ± 3.5 | 38.5 ± 4.2 | 45.1 ± 4.5 |
| 4h | 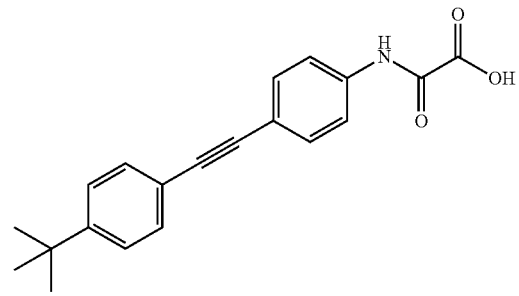 [SMILES: CC(C)(C)c1ccc(C#Cc2ccc(NC(=O)C(=O)O)cc2)cc1] | 0.026 ± 0.005 | >50 | >50 | >50 |
| 4i | 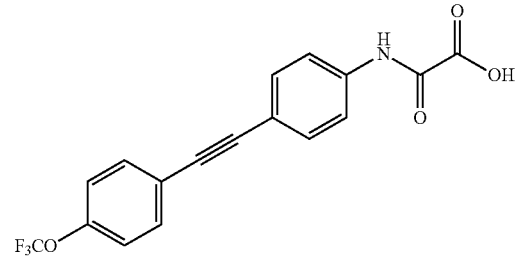 [SMILES: O=C(O)C(=O)Nc1ccc(C#Cc2ccc(OC(F)(F)F)cc2)cc1] | 0.027 ± 0.001 | >50 | >50 | >50 |

TABLE 2-continued

IC$_{50}$ values fo compound 4, 4a-4s against a panel of PTPs

| Entry | Structure | mPTPB IC$_{50}$ (μM) | SHP2 IC$_{50}$ (μM) | SHP1 IC$_{50}$ (μM) | PTP1B IC$_{50}$ (μM) |
| --- | --- | --- | --- | --- | --- |
| 4j | [3-CF$_3$-phenyl-C≡C-phenyl-NHC(O)C(O)OH] | 0.053 ± 0.011 | >50 | >50 | 29.5 ± 4.1 |
| 4k | [4-CF$_3$-phenyl-C≡C-phenyl-NHC(O)C(O)OH] | 0.015 ± 0.003 | >50 | >50 | >50 |
| 4l | [4-H$_2$NSO$_2$-phenyl-C≡C-phenyl-NHC(O)C(O)OH] | 0.088 ± 0.007 | >50 | 29.9 ± 3.3 | >50 |
| 4m | [4-HO-phenyl-C≡C-phenyl-NHC(O)C(O)OH] | 0.106 ± 0.014 | >50 | >50 | >50 |
| 4n | [3-Br-4-HO-phenyl-C≡C-phenyl-NHC(O)C(O)OH] | 0.033 ± 0.002 | 44.5 ± 3.4 | >50 | >50 |

TABLE 2-continued

IC$_{50}$ values fo compound 4, 4a-4s against a panel of PTPs

| Entry | Structure | mPTPB IC$_{50}$ (μM) | SHP2 IC$_{50}$ (μM) | SHP1 IC$_{50}$ (μM) | PTP1B IC$_{50}$ (μM) |
|---|---|---|---|---|---|
| 4o | 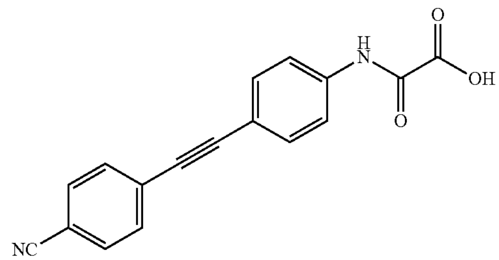 [SMILES: N#Cc1ccc(C#Cc2ccc(NC(=O)C(=O)O)cc2)cc1] | 0.129 ± 0.014 | >50 | >50 | >50 |
| 4p | 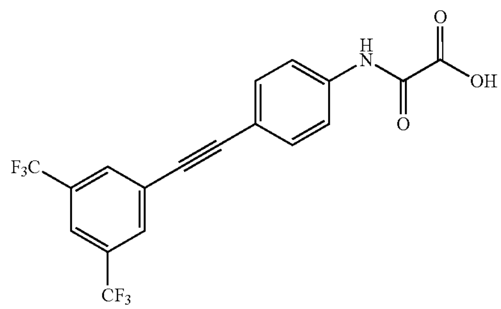 [SMILES: O=C(O)C(=O)Nc1ccc(C#Cc2cc(C(F)(F)F)cc(C(F)(F)F)c2)cc1] | 0.060 ± 0.009 | >50 | >50 | >50 |
| 4q | 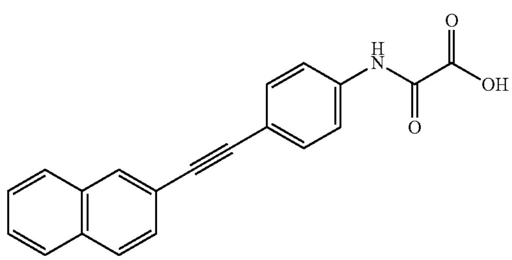 [SMILES: O=C(O)C(=O)Nc1ccc(C#Cc2ccc3ccccc3c2)cc1] | 0.093 ± 0.005 | >50 | >50 | >50 |
| 4r | 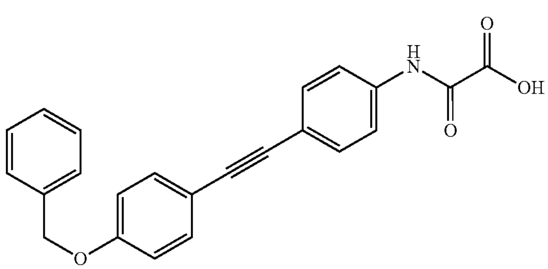 [SMILES: O=C(O)C(=O)Nc1ccc(C#Cc2ccc(OCc3ccccc3)cc2)cc1] | 0.038 ± 0.006 | 15.3 ± 2.1 | 16.8 ± 3.3 | 38.9 ± 5.0 |
| 4s | 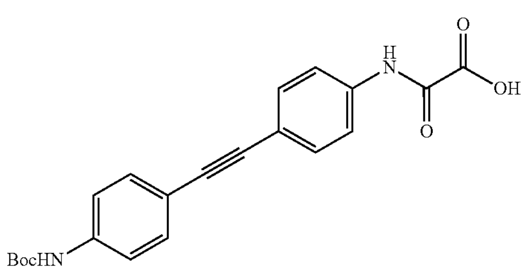 [SMILES: CC(C)(C)OC(=O)Nc1ccc(C#Cc2ccc(NC(=O)C(=O)O)cc2)cc1] | 0.035 ± 0.002 | >50 | >50 | >50 |

After obtaining potent inhibitor 4k with an IC$_{50}$ of 15 nM for mPTPB, efforts were sought to further improve its activity through the installation of additional substituents in the distal phenyl ring. Halogens, mainly the lighter ones fluorine and chlorine, Compounds containing chlorine, bromine, or iodine can form interactions of the type R-X • • • Y-R (halogen bond), where X is the halogen (acts as a Lewis acid), and Y can be any electron donor moiety. In protein-ligand environments, halogen bonds can be formed between a halogen atom in the ligand and any nearby Lewis base in the protein, such as backbone carbonyl oxygen. Additionally, halogen bonds can be formed with groups present in the side chains, such as —OH (Ser, Thr, and Tyr), —COOH (Asp and Glu), sulfur (Cys and Met), nitrogen (His) and the a surfaces (Tyr, Phe, Try, and His). Moreover, halogens such as fluorine are known to alter the physicochemical properties of compounds and increase the metabolic stability of drug molecules. To this end, compounds 4t, 4u and 4v were synthesized with chlorine, bromine and fluorine atoms meta to the $CF_3$ in 4k, respectively. This resulted in compounds with improved affinity (Table 3). Analogs 4t and 4u demonstrated-2-fold improvement in binding compared to 4k, which also represents a 44-fold increase in activity compared to parent compound 4 (Table 2). Though, both 4t and 4u showed similar affinity towards mPTPB, 4t showed superior aqueous solubility, Log D, c Log P, and selectivity (Table 4). On the other hand, nitrile containing analog, 4w demonstrated a decrease in potency compared to 4k.

TABLE 3

$IC_{50}$ values of 4k analogs against a panel of PTPs

| Entry | Structure | mPTPB $IC_{50}$ (μM) | SHP2 $IC_{50}$ (μM) | SHP1 $IC_{50}$ (μM) | PTP1B $IC_{50}$ (μM) |
|---|---|---|---|---|---|
| 4t | 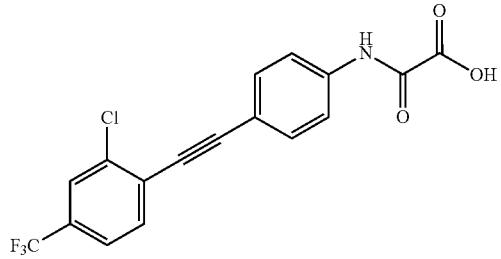 [SMILES: O=C(O)C(=O)Nc1ccc(C#Cc2ccc(C(F)(F)F)cc2Cl)cc1] | 0.0064 ± 0.0005 | >30 | >30 | >30 |
| 4u | 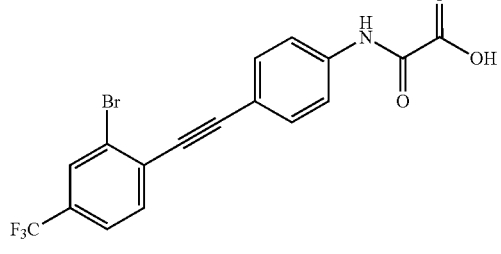 | 0.0041 ± 0.0017 | 15.2 ± 3.4 | 33.8 ± 6.8 | 16.4 ± 2.9 |
| 4v | 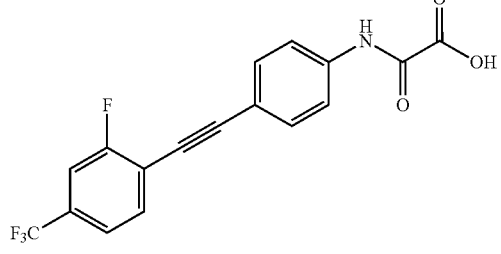 | 0.012 ± 0.003 | >30 | >30 | >30 |
| 4w | 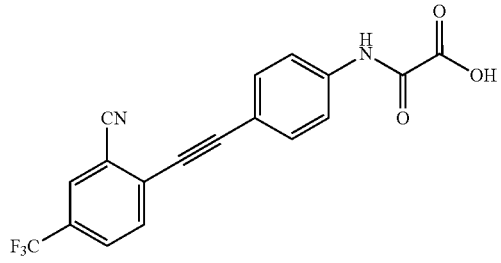 [SMILES: O=C(O)C(=O)Nc1ccc(C#Cc2ccc(C(F)(F)F)cc2C(F)(F)F)cc1] | 0.023 ± 0.001 | 10.6 ± 2.5 | 13.7 ± 3.1 | 27.4 ± 6.3 |

TABLE 3-continued

IC$_{50}$ values of 4k analogs against a panel of PTPs

| Entry | Structure | mPTPB IC$_{50}$ (μM) | SHP2 IC$_{50}$ (μM) | SHP1 IC$_{50}$ (μM) | PTP1B IC$_{50}$ (μM) |
|---|---|---|---|---|---|
| 4x | 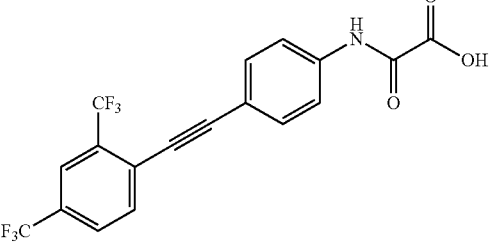 | 0.014 ± 0.002 | >30 | >30 | >30 |

TABLE 4

Calculated and determined physicochemical properties of selected compounds

| Compound | MW$^a$ | tPSA$^b$ | CLogp$^c$ | LogD$^d$ | Aq. Sol (μM)$^e$ | LE$^f$ | LLE$^g$ | Microsome Stability$^h$ |
|---|---|---|---|---|---|---|---|---|
| 4b | 339 | 112.9 | 1.96 | 1.94 | 38.6 | 0.42 | 5.64 | NT |
| 4h | 321 | 66.4 | 3.50 | 2.32 | 18.4 | 0.43 | 5.26 | 27 ± 2.4 |
| 4k | 333 | 66.4 | 2.69 | 1.97 | 22.4 | 0.44 | 5.85 | 38 ± 1.6 |
| 4t | 368 | 66.4 | 3.29 | 1.84 | 67.3 | 0.45 | 6.31 | 56 ± 1.5 |
| 4u | 412 | 66.4 | 3.42 | 2.28 | 24.6 | 0.46 | 6.12 | 60 ± 3.8 |
| 4v | 351 | 66.4 | 2.78 | 1.81 | 33.5 | 0.43 | 6.11 | 72 ± 2.8 |

$^a$Molecular weight.
$^b$Topological polar surface area (Å$^2$).
$^c$molinspiration calculated LogP.
$^d$LogD was experimentally determined using shake flask method (n-octanol and pH 7.4 PBS).
$^e$Kinetic solubilities measured in pH 7.4 PBS buffer.
$^f$Ligand efficiency calculated using the equation: LE = −1.37 Å × log(potency(M))/heavy atom count.
$^g$Lipophilic ligand efficiency calculated using the equation: LLE = −log(potency (M)) − LogD.
$^h$Mouse, % remaining after 60 min at 37° C. (reactions were run in duplicate).
NT = not tested.

Finally, to evaluate the importance of triple bond, compounds with a double bond or a single bond were prepared using hydrogenation reaction (Table 5). To synthesize compounds 9 and 10, Lindlar catalyst (5% Pd/BaSO$_4$, quinoline, H$_2$ gas) was used. On the other hand, 10% Pd/C, methanol, and H$_2$ gas were used to synthesize the single bond containing analogs 11 and 12 (Scheme 3). The potency of the double bond or single bond containing derivatives dramatically decreased. Compounds 9 and 10 showed 3 and 45-fold less potency compared to their corresponding alkyne analogs 4 and 4k, respectively. Similarly, compounds 11 and 12 showed 5 and 13-fold less activity compared to 4 and 4k, respectively. These observations indicate the importance of rigidity and directionality of the triple bonded substitutions at the para position of the N-aryloxamic acid core for optimal interaction with mPTPB.

Scheme 3. Synthesis of alkene and alkane-based derivatives of 4 and 4k.

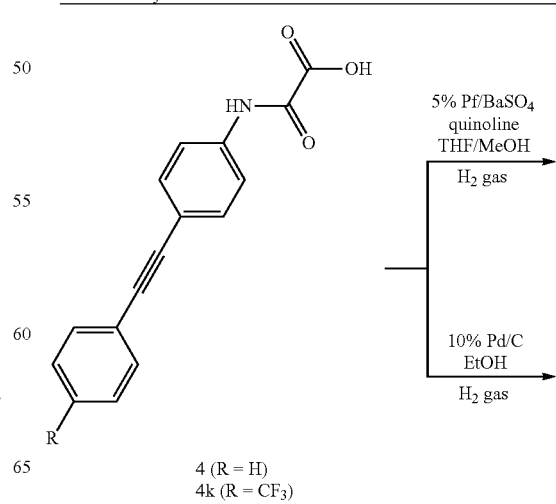

-continued
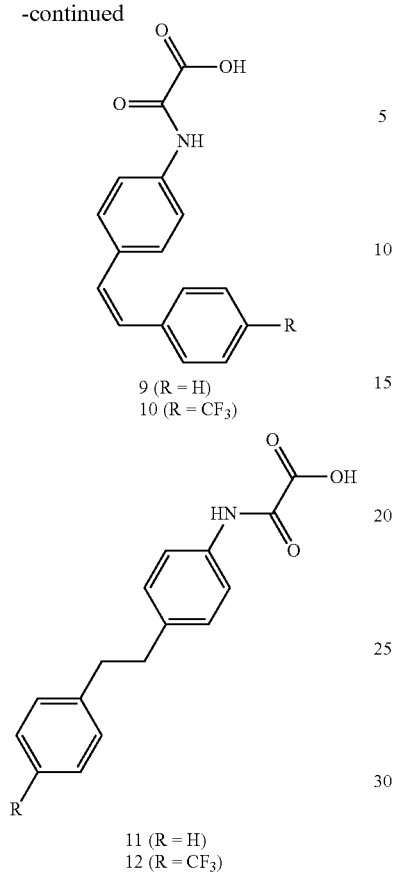
9 (R = H)
10 (R = CF₃)
11 (R = H)
12 (R = CF₃)
TABLE 5
IC$_{50}$ values of alkene and alkane containing analogs of 4 and 4k against mPTPB, SHP2 and PTP1B.
| Entry | Structure | IC$_{50}$ (μM) mPTPB | IC$_{50}$ (μM) SHP2 | IC$_{50}$ (μM) PTP1B |
|---|---|---|---|---|
| 9 | 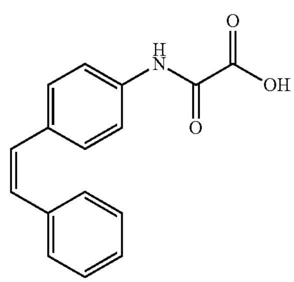 [SMILES: O=C(O)C(=O)Nc1ccc(/C=C\c2ccccc2)cc1] | 0.770 ± 0.015 | >30 | >30 |
| 10 | 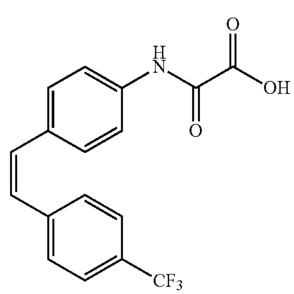 [SMILES: O=C(O)C(=O)Nc1ccc(/C=C\c2ccc(C(F)(F)F)cc2)cc1] | 0.684 ± 0.025 | >30 | >30 |

TABLE 5-continued

IC$_{50}$ values of alkene and alkane containing analogs of 4 and 4k against mPTPB, SHP2 and PTP1B.

| Entry | Structure | IC$_{50}$ (μM) mPTPB | IC$_{50}$ (μM) SHP2 | IC$_{50}$ (μM) PTP1B |
|---|---|---|---|---|
| 11 | 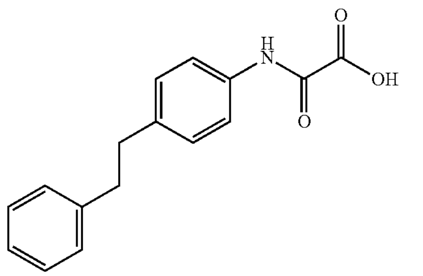 [SMILES: O=C(O)C(=O)Nc1ccc(CCc2ccccc2)cc1] | 1.27 ± 0.20 | >30 | >30 |
| 12 | 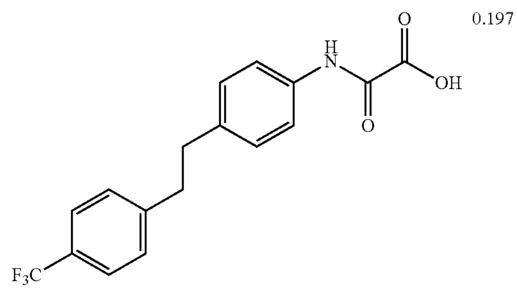 | 0.197 ± 0.013 | >30 | >30 |

Inhibitor Selectivity Studies.

In order to enable pharmacological assessment of mPTPB as a novel anti-TB target, the specificity of mPTPB inhibitor is of utmost importance. Compounds 4g, 4k and 4t were subjected to specificity profiling for mPTPB versus a large panel of PTPs, including the bacterial PTPs, mTPTPA (the only other PTP in the Mtb genome) and YopH from *Yersinia*, the non-receptor PTPs, SHP1, SHP2, PTP1B, TC-PTP, MEG2, HePTP, STEP, FAP1, and LYP, the receptor-like PTPs, CD45, PTPσ, PTPα, PTPgμ, PTFγ, and PTPε, and the dual specificity phosphatases (DSPs) Laforin, VHR, MKP3, MKP5 and Cdc14A. Compound 4g was subjected to specificity profiling for mPTPB versus a panel of over 25 PTPs. This compound showed no inhibition against majority of PTPs even at 50 μM, except SHP1, SHP2, PTP1B, LMWPTP and PTPP (Table 5). On the other hand, when screened at 30 μM, compounds 4k and 4t showed no inhibition against PTPs tested, suggesting selectivity greater than 2,000 and 4,500-fold for mPTPB over other PTPs, respectively.

The mode of mPTPB inhibition by these compounds was determined in a kinetic assay, varying the substrate pNPP and inhibitor concentrations. Lineweaver Burk plots of these inhibitors revealed them as classic competitive inhibitors, affecting the apparent K$_m$ value, while V$_{max}$ was unchanged. This observation is consistent with the expectation that these compounds bind to the active site of mPTPB, due to the pTyr mimetic properties of N-aryl oxamic acid moiety. Compounds 4t, 4u, and 4v, showed inhibition constant (K$_i$) values of 2.7±0.2, 1.2±0.1, and 4.9±0.6 nM, respectively. To rule out the possibility of promiscuous inhibition, IC$_{50}$ experiments for 4p and 4v were conducted with and without 0.01% (v/v) of Triton X-100 in the buffer and time-dependent inhibition (enzyme and inhibitor were preincubated for 30 mins prior to IC$_{50}$ determination). These experiments showed no significant difference in the IC$_{50}$ values of the inhibitors tested, suggesting them as a valid active site directed inhibitors for mPTPB.

Molecular Docking Studies.

To understand the potential interactions between these inhibitors and mPTPB, molecular docking studies was conducted using Glide. The active site structures of PTPs are positively charged, which facilitates its interaction with negatively charged molecules, such as pTyr mimetics with high affinity. All PTPs share a conserved active site signature motif of HCX$_5$R, in the catalytic domain of about 240 amino acids. The phosphate-binding loop (P-loop) harbors the catalytic cysteine (Cys160 in mPTPB) within the HCX$_5$R motif. The P-loop sequence of HCFAGKDR is unique to mPTPB and differentiates this enzyme from other members of the PTP family. Compared to its mammalian FTP counterparts, mPTPB has a relatively deeper and broader active site, which is consistent with its phosphoinositide activity. The polar oxamic acid head group occupies the P-loop pocket with various polar interactions, and the hydrophobic distal phenyl ring bearing CF$_3$ fills the hydrophobic pocket. As predicted by the modeling work, inhibitor 4t binds into the active site pocket of mPTPB, makes key hydrogen-bonding interactions with P-loop residues, Phe161, Ala162, Lys164, Asp165, and Arg166. The oxalamide group forms an intricate network of hydrogen bonds to Asp165, Arg166, the backbone of Phe161, Gly-163, and Asp165. In mPTPB, Phe161 is adjacent to the catalytic cysteine making hydrophobic contacts with the phenyl ring in 4t, whereas the human PTPs such as PTP1B, SHP1, SHP2, TcPTP, and HePTP have a Ser in this position. Most importantly, three of the P-loop amino acids Phe161, Lys164, and Asp165 that make H-bonding interactions with 4t are not present in other mammalian PTPs. The internal alkyne provides the required space between the two aromatic rings, which allows the distal benzene ring to make hydrophobic interactions with Phe98. In addition, the fluorine atoms in CF$_3$ of 4t are making favorable interactions with a hydrophobic pocket (Ile203, Met206, and Ile207). So, the high affinity of 4k, 4t, 4u, and 4v, can be attributed to the proposed hydrophobic interactions of the fluorine atoms in $CF_3$ with the hydrophobic pocket. Thus, these molecules achieve their high potency and selectivity by exploiting the non-conserved regions in both hydrophilic and hydrophobic regions in the mPTPB active site. The above observations suggest that these compounds are expected to show specificity towards mPTPB over other PTPs in addition to the ones screened here (Table 6).

TABLE 6

The specificity of 4g, 4k and 4t for mPTPB over a large panel of PTPs

| PTP | 4g $IC_{50}$ (μM) | 4k $IC_{50}$ (μM) | 4t $IC_{50}$ (μM) |
| --- | --- | --- | --- |
| mPTPB | 0.160 | 0.015 | 0.0064 |
| mPTPA | >50 | >50 | >30 |
| SHP1 | 38.5 | >50 | >30 |
| SHP2 | 47.5 | >50 | >30 |
| PTP1B | 45.1 | >50 | >30 |
| TC-PTP | >50 | >50 | >30 |
| LYP | >50 | >50 | >30 |
| HePTP | >50 | >50 | >30 |
| FAP-1 | >50 | >30 | >30 |
| DEP-1 | >50 | >30 | >30 |
| Laforin | >50 | >30 | >30 |
| PTP-MEG2 | >50 | >30 | >30 |
| MKP3 | >50 | >30 | >30 |
| MKP5 | >50 | >30 | >30 |
| YopH | >50 | >30 | >30 |
| LMPTP-1 | 34.5 | >30 | >30 |
| PTP-PEST | >50 | >30 | >30 |
| CD45 | >50 | >30 | >30 |
| CDC14A | >50 | >30 | >30 |
| STEP | >50 | >30 | >30 |
| VHR | >50 | >30 | >30 |
| PTPσ | >50 | >30 | >30 |
| PTPα | >50 | >30 | >30 |
| PTPβ | 11.5 | >30 | >30 |
| PTPμ | >50 | >30 | >30 |
| PTPγ | >50 | >30 | >30 |
| PTPε | >50 | >30 | >30 |

Physicochemical Properties

Given the excellent potency and selectivity of these inhibitors, the physicochemical properties were measured for selected compounds. Physicochemical properties such as, topological polar surface area (tPSA), c Log P, Log D, and aqueous solubility of 4b, 4h, 4k, 4t, 4u, and 4v were shown in Table 4. All these compounds showed moderate aqueous solubility in the range of 18 to 68 μM (pH=7.4 PBS buffer). It has been proposed that ligand efficiency (LE) may be a method for comparing molecules according to their average binding energy per heavy atom. It is a powerful tool for assessing the quality of ligand molecules, as larger molecules tend to show better potency due to the larger number of interactions, but may not necessarily be the most efficient. Hence, smaller but more efficient molecules are needed as they have a higher probability of successfully advancing in the lead optimization process. Lipophilic ligand efficiency (LLE), is an estimate of the specificity of a molecule in binding to the target relative to partitioning into n-octanol. The proposed acceptable values of LE and LLE for drug candidates are LE>0.3 and LLE>5. All the compounds shown in Table 4 show LE values of >0.42 and LLE values of >5.3. Importantly, these compounds also follow the GSK 4/400 rule (higher risks of off-target interactions and toxicity, if MW >400 and c Log P >4), suggesting that they could serve as potential candidates for drug development.

An ideal compound for the mouse in vivo studies should be soluble, have good absorption, and must exhibit metabolic stability. A sufficient oral dosage must survive first-pass clearance through the liver before reaching its biological target. The majority of drugs/xenobiotics undergo phase I metabolism, mediated by the cytochrome P450 (CYP450) family of heme-thiolate proteins predominantly in the liver. Although mouse liver microsomal (MLM) stability studies are not a perfect substitute for in vivo metabolic clearance studies, but they serve as an initial cell-based model system that can correlate well with human liver microsomal (HLM) stability and in vivo activity in mice. To this end, compounds 4h, 4k, 4t, 4u, and 4v were allowed to react with mouse liver microsomes and the fraction of remaining parent compound over time was determined. Compound 4h with a tert-butyl was the least stable as measured by the last time point compared to all other compounds with $CF_3$. Incorporation of fluorine into drug candidates generally improves their potency, bioavailability, and metabolic stability. In addition, fluorinated molecules are in general, nontoxic and mimic the corresponding nonfluorinated analogs in their stereoelectronic properties, so the drug's affinity for the receptor either remains the same or, in some cases increases. The improved metabolic stability of $CF_3$ containing 4k, 4t, 4u and 4v compared to 4h, partly due to the stronger C—F bond compared to C—H (116 and 99 kcal mol$^{-1}$, respectively), which makes the C—F bond less sensitive to metabolic degradation. Importantly, the analysis of co-factor absent microsome reactions suggests that all these analogs are stable at 37° C. for one hour. So, the loss of compounds tested here is attributed only to oxidative Phase I metabolism. The high microsomal stability of these compounds could be exploited pharmacologically.

Cell Permeability Studies.

Cell permeability is the major hurdle in the development of active site directed PTP inhibitors. The majority of the pTyr mimetics reported, carry one or more negative charges for binding with the positively charged PTP active site, are deficient in cell membrane permeability, which limits further advancement of such compounds as drug candidates. Raw264.7 cells were treated with compounds 4k, 4t, 4u, and 4v and determined the cell permeability potential of our compounds using LC-MS based method. The cellular bioavailability studies indicated that these compounds can easily be taken up by Raw264.7 cells.

Cellular Activity of Compound 4t in Blocking mPTPB-Mediated Signaling

After evaluating the cell permeability of these compounds in Raw264.7 cells, compound 4t's cellular efficacy was investigated. Once inside the host macrophage, mPTPB activates Akt signaling and blocks ERK1/2 and p38 activation to prevent macrophage apoptosis and increase cytokine production. As found, compound 4t increased the IFN-γ induced phosphorylation of ERK1/2 and p38 but reduced Akt activity in mPTPB transfected Raw264.7 cells in a dose-dependent manner. The observation that 4t phenocopied several structurally unrelated small molecule mPTPB inhibitors in cell-based assays strongly suggest that the detected cellular effects of 4t in macrophages are indeed from specific inhibition of mPTPB. Of particular note is the finding that 4t's cellular activity tracked very well with its $IC_{50}$ value measured with purified recombinant mPTPB in biochemical assays. Together, these results indicate that 4t is highly efficacious in blocking mPTPB activity inside the cell.

Conclusions

Given the importance of PTPs in regulating cellular singling and homeostasis, there is increasing interest in developing PTP-based therapeutics for a wide range of diseases including cancer, diabetes, autoimmune disorders, and infectious diseases. As a key virulence factor for Mtb survival within host macrophages, mPTPB has garnered substantial attention as a novel anti-TB target. Importantly, the absence of a human orthologue for mPTPB makes it a highly attractive target for the development of novel anti-TB candidates. However, the acquisition of highly potent, specific, and efficacious PTP inhibitors with properties suitable for in vivo experiments and clinical translation has proven to be difficult, primarily due to the highly conserved and positively charged nature of the PTP active sites. This disclosure has shown that through fragment-based approaches, negatively charged pTyr mimetics such as salicylic acids and α-sulfophenylacetic amide can be transformed into highly potent and selective active site-directed PTP inhibitors with robust in vivo efficacy. Nevertheless, the design of minimally charged, stable, and high affinity non-hydrolyzable pTyr surrogate has generally met with limited success, and this presents a major challenge to the development of novel therapeutics based on the PTPs.

Here, this disclosure has identified N-phenyl oxamic acid as a highly potent and selective monoacid-based pTyr mimetic for mPTPB inhibition. SAR studies were conducted by varying the substituents on the phenyl ring and discovered 4-phenylethynyl containing analog (compound 4) as the best core structure for further modification. Several mono-, di-, and trisubstituted analogs of compound 4 were synthesized, among them, compound 4t showed a $K_i$ of 2.7 nM for mPTPB with >4,500-fold preference over 25 PTPs. Kinetic and molecular docking analysis confirmed these compounds as active site-directed reversible inhibitors of mPTPB. Importantly, these N-phenyl oxamic acid inhibitors penetrate cell membranes and inhibit mPTPB inside the cells. These oxamic acid-based inhibitors are capable of reversing the altered host cell immune responses induced by the bacterial phosphatase. Furthermore, the reported mPTPB inhibitors possess highly compact structures with molecular weights <400 Da, c Log P<4, Log D7.4<2.5, LE>0.42 and with favorable drug-like properties. Collectively, the results indicate that the N-phenyl oxamic acid pharmacophore is sufficiently polar to bind the FTP active site, yet remain capable of efficiently crossing cell membranes, offering FTP inhibitors with both high affinity and selectivity and excellent cellular efficacy. The results also provide another example of developing minimally charged, highly potent and selective active site directed PTP inhibitors by exploiting the specific structural features of the active sites of different PTPs. This work not only offers further opportunities to evaluate mPTPB inhibition as a tuberculosis treatment but also should stimulate interest in targeting other mPTPB orthologues, which are present in over 50 human pathogens, including *Listeria monocytogenes*.

Experimental Section

General synthetic procedures and reagents. Unless otherwise noted, all reagents were purchased from commercial suppliers and used without further purification. Thin-layer chromatography (TLC) was performed using glass pre-coated Merck silica gel 60 $F_{254}$ plates. Column chromatography was performed using KP-SIL silica gel (Biotage, USA), and flash column chromatography was performed on Biotage prepacked columns using the automated flash chromatography system Biotage Isolera One. Organic solvents were evaporated using rotary evaporation at 40-45° C. The $^1$H- and $^{13}$C NMR spectra were recorded on a Bruker AVANCE 500 MHz spectrometer using $CDCl_3$ or DMSO $(d_6)$ as the solvent. Chemical shifts are expressed in ppm (δ scale) and referenced to residual protonated solvent. Peak multiplicities are reported using the following abbreviations: s (singlet), d (doublet), t (triplet), q (quartet), m (multiplet), or br (broad singlet). Low-resolution mass spectra and purity data were obtained using an Agilent Technologies 6470 series, triple quadrupole LC/MS. The purity of all final tested compounds was determined to be >95% (UV, λ=254 nm). High-Resolution Mass analysis was performed on an Agilent 6550 iFunnel Q-TOF mass LC/MS.

Synthesis of Oxanilic Acid (1)

To a stirred solution of aniline (300 mg, 3.22 mmol) and N,N-diisopropyl ethylamine (1.11 mL, 6.44 mmol) in 15 mL of anhydrous $CH_2Cl_2$ was added methyl chlorooxoacetate (327 μL, 3.54 mmol) drop-wise. The resulting solution was stirred at room temperature under $N_2$ gas for 30 min. The reaction mixture was washed with 15 mL of DI water and 15 mL of brine. The organic layer was dried over anhydrous $Na_2SO_4$ and evaporated in vacuo. Crude ester subjected for hydrolysis using 12 mL of 1N KOH/THF (1:1 v/v) at room temperature for 1 hour. After completion, THF evaporated and aqueous layer acidified to pH~2 using 3N HCL and resulting solid filtered. Column chromatographic purification of the residue using silica and 10% methanol in dichloromethane as eluent afforded product as a white solid (490 mg, 92% yield). $^1$H NMR (DMSO-$d_6$, 500 MHz) δ 10.68 (s, 1H), δ 7.74 (d, J=7.5 Hz, 2H), δ 7.33 (t, J=7.5 Hz, 2H), δ 7.11 (t, J=7.5 Hz, 1H); $^{13}$C NMR (DMSO-$d_6$, 125 MHz) δ 162.6, 157.3, 138.1, 129.2, 125.0, 120.8; Mass spectra (ESI): m/e 164 (M–H)$^-$. HRMS (ESI-TOF, [M–H]$^-$) m/z calcd for $C_8H_6NO_3$ 164.0348, found 164.0354.

Synthesis of methyl 2-((4-ethynylphenyl)amino)-2-oxoacetate (Core 1)

To an ice-cold solution of 4-ethynylphenylamine (4.0 g, 34.14 mmol) and N,N-diisopropyl ethylamine (11.82 mL, 68.29 mmol) in 100 mL of anhydrous $CH_2Cl_2$ was added methyl chlorooxoacetate (3.46 mL, 37.56 mmol) drop-wise under $N_2$ atmosphere. The resulting solution was stirred at room temperature for 1 hour. The reaction mixture was washed with 100 mL of DI water and 100 mL of brine. The organic layer was dried over anhydrous $Na_2SO_4$ and evaporated in vacuo. The product was then purified by column chromatography on silica gel using a mixture of ethylacetate-hexanes as eluent. White powder; (6.2 g, 96% yield). $^1$H NMR (DMSO-$d_6$, 500 MHz) δ 10.94 (s, 1H), δ 7.77 (d, J=9.0 Hz, 2H) δ 7.45 (d, J=9.0 Hz, 2H), δ 4.11 (s, 1H), δ 3.84 (s, 3H); $^{13}$C NMR (DMSO-$d_6$, 125 MHz) δ 161.3, 155.7, 138.5, 132.8, 120.8, 118.2, 83.7, 80.9, 53.7. Mass spectra (ESI): m/e 202 (M–H)$^-$. HRMS (ESI-TOF, [M–H]$^-$) m/z calcd for $C_{11}H_9NO_3$ 202.0504, found 202.0510.

Synthesis of methyl 2-((3-ethynylphenyl)amino)-2-oxoacetate (Core 2)

To an ice-cold solution of 3-ethynylphenylamine (2.0 g, 17.07 mmol) and N,N-diisopropyl ethylamine (5.91 mL, 34.14 mmol) in 50 mL of anhydrous $CH_2Cl_2$ was added methyl chlorooxoacetate (1.73 mL, 18.78 mmol) drop-wise under $N_2$ atmosphere. The resulting solution was stirred at room temperature for 1 hour. The reaction mixture was washed with 50 mL of DI water and 50 mL of brine. The organic layer was dried over anhydrous $Na_2SO_4$ and evaporated in vacuo. The product was then purified by column chromatography on silica gel eluted with a mixture of ethylacetate-hexanes. Off-white powder; (3.0 g, 93% yield). $^1$H NMR (DMSO-$d_6$, 500 MHz) δ 10.88 (s, 1H), δ 7.90 (s, 1H), δ 7.75-7.77 (m, 1H) δ 7.35 (t, J=8.0 Hz, 1H), δ 7.24 (d, J=7.5 Hz, 1H), δ 4.18 (s, 1H), δ 3.84 (s, 3H); $^{13}$C NMR (DMSO-$d_6$, 125 MHz) δ 161.3, 155.8, 138.2, 129.7, 128.4, 123.7, 122.5, 121.6, 83.6, 81.3, 53.7. Mass spectra (ESI): m/e 202 (M−H)$^-$. HRMS (ESI-TOF, [M−H]$^-$) m/z calcd for $C_{11}H_9NO_3$ 202.0504, found 202.0510.

Synthesis of methyl 2-((4-iodophenyl)amino)-2-oxoacetate (Core 3)

To an ice-cold solution of 4-iodoaniline (3.0 g, 13.7 mmol) and N,N-diisopropyl ethylamine (3.0 mL, 20.55 mmol) in 60 mL of anhydrous $CH_2Cl_2$ was added methyl chlorooxoacetate (1.5 mL, 16.44 mmol) drop-wise under $N_2$ atmosphere. The resulting solution was stirred at room temperature for 1 hour. The reaction mixture was washed with 60 mL of DI water and 60 mL of brine. The organic layer was dried over anhydrous $Na_2SO_4$ and evaporated in vacuo. The product was then purified by column chromatography on silica gel eluted with a mixture of ethylacetate-hexanes. White powder; (4.0 g, 96% yield). $^1$H NMR (DMSO-$d_6$, 500 MHz) δ 10.88 (s, 1H), δ 7.68 (d, J=8.5 Hz, 2H), δ 7.57 (d, J=8.5 Hz, 2H), δ 3.83 (s, 3H); $^{13}$C NMR (DMSO-$d_6$, 125 MHz) δ 161.3, 155.7, 137.9, 137.8, 123.0, 89.4, 53.7. Mass spectra (ESI): m/e 304 (M−H)$^-$.

Synthesis of 2-((4-ethynylphenyl)amino)-2-oxoacetic Acid (2)

A stirred solution of core 1 (100 mg) in 8 mL of 1N KOH/THF (1:1 v/v) was stirred at room temperature for 1 hour. After completion, THF completely evaporated and aqueous layer acidified to pH~2 using 3N HCL and resulting solid filtered to yield pure compound 2 as an off-white solid (90 mg, 95% yield). $^1$H NMR (DMSO-$d_6$, 500 MHz) δ 10.85 (s, 1H), δ 7.78 (d, J=8.5 Hz, 2H), δ 7.44 (d, J=8.5 Hz, 2H), δ 4.11 (s, 1H); $^{13}$C NMR (DMSO-$d_6$, 125 MHz) δ 162.4, 157.5, 138.7, 132.8, 120.6, 117.9, 83.8, 80.9. Mass spectra (ESI): m/e 188 (M−H)$^-$.

Synthesis of 2-((4-(3-((tert-butoxycarbonyl)amino)prop-1-yn-1-yl)phenyl)amino)-2-oxoacetic Acid (3)

To a stirred solution of methyl 2-((4-iodophenyl)amino)-2-oxoacetate (400 mg, 1.0 eq.) in 5 mL of anhydrous DMF was added the tert-butyl prop-2-yn-1-ylcarbamate (224 mg, 1.1 eq.), sodium carbonate (278 mg, 2.0 eq.), $Pd(PPh_3)_2Cl_2$ (5 mol %), and copper iodide (5 mol %), the resulting mixture stirred at room temperature under $N_2$ atmosphere. Reactions were monitored by LC-MS. After completion of the reaction, DMF was completely removed using high-vac. The residue was dissolved in 70 mL of ethyl acetate and washed with 50 mL of DI water. The organic layer was dried over anhydrous $Na_2SO_4$ and evaporated the solvent. Crude ester subjected for hydrolysis using 1N KOH/THF (1:1 v/v) at room temperature for 1 hour. After completion, THF evaporated and aqueous layer acidified to pH~3 using cold 1N HCL and resulting solid filtered. Compound 3 was purified by column chromatography using a mixture of methanol-dichloromethane as eluent on silica gel (stationary phase) as an off-white powder (351 mg, 84% yield). $^1$H NMR (DMSO-$d_6$, 500 MHz) δ 10.59 (s, 1H), δ 7.76 (d, J=8.5 Hz, 2H), 7.33 (d, J=8.5 Hz, 2H), 3.94 (d, J=5.5 Hz, 2H), δ 1.38 (s, 9H); $^{13}$C NMR (DMSO-$d_6$, 125 MHz) δ 162.8, 160.4, 155.8, 138.8, 132.3, 120.2, 117.9, 87.4, 81.9, 78.7, 30.6, 28.7; Mass spectra (ESI): m/e 317 (M−H)$^-$. HRMS (ESI-TOF, [M−H]$^-$) m/z calcd for $C_{16}H_{17}N_2O_5$ 317.1132, found 317.1134.

General Procedure for the Synthesis of Compounds 4, 4a-4x, and 5.

To a stirred solution of methyl 2-((4-ethynylphenyl)amino)-2-oxoacetate (200 mg, 1.0 eq.) in 3 mL of anhydrous DMF was added the aryl iodides (1.1 eq.), sodium carbonate (2.0 eq.), $Pd(PPh_3)_2Cl_2$ (5 mol %), and copper iodide (5 mol %), the resulting mixture stirred at room temperature under $N_2$ atmosphere. Reactions were monitored by LC-MS. After completion of the reaction, DMF was completely removed using high-vac. The residue was dissolved in 50 mL of ethyl acetate and washed with 40 mL of DI water. The organic layer was dried over anhydrous $Na_2SO_4$ and evaporated the solvent. Crude ester subjected for hydrolysis using 1N KOH/THF (1:1 v/v) at room temperature for 1 hour. After completion, THF evaporated and aqueous layer acidified to pH~2 using 3N HCL and resulting solid filtered. Products were then purified by column chromatography on silica gel eluted with mixture of methanol-dichloromethane.

General Procedure for Preparation of Compounds 9 and 10.

To a stirred solution of 4 or 4k (50 mg) in 4 mL of THF/methanol (1:1 v/v) was added 5 mg of 5% Pd/BaSO$_4$ and 50 µL of quinoline, then the mixture was allowed to stir for 12 h at room temperature under $H_2$ atmosphere. After completion of the reaction (monitored by LC-MS), the mixture was filtered through Celite pad, and the filtrate was concentrated under reduced pressure. The residue was purified by column chromatography using methanol/dichloromethane mixture as eluent to furnish compounds 9 and 10 in >70% yields.

General Procedure for Preparation of Compounds 11 and 12.

To a stirred solution of 4 or 4k (50 mg) in ethanol (4 mL) was added 5 mg of 10% Pd/C, and the mixture was allowed to stir for 4 h at room temperature under $H_2$ atmosphere. After completion of the reaction (monitored by LC-MS), the mixture was filtered through Celite pad, and the filtrate was concentrated under reduced pressure. The residue was purified by column chromatography using methanol/dichloromethane mixture as eluent to furnish compounds 11 and 12 in >90% yields.

2-oxo-2-((4-(phenylethynyl)phenyl)amino)acetic Acid (4)

White solid; (235 mg, 90% yield). $^1$H NMR (DMSO-$d_6$, 500 MHz) δ 10.62 (s, 1H), δ 7.82 (d, J=8.5 Hz, 2H), δ 7.48-7.53 (m, 4H), δ 7.38-7.41 (m, 3H); $^{13}$C NMR (DMSO-$d_6$, 125 MHz) δ 162.7, 160.7, 139.2, 132.2, 131.7, 129.2, 129.1, 122.9, 120.2, 117.7, 89.9, 89.2. Mass spectra (ESI): m/e 264 (M−H)$^-$. HRMS (ESI-TOF, [M−H]$^-$) m/z calcd for $C_{16}H_{10}NO_3$ 264.0661, found 264.0670.

2-((4-((4-(methoxycarbonyl)phenyl)ethynyl)phenyl)amino)-2-oxoacetic Acid (4a)

White powder; (249 mg, 78% yield). $^1$H NMR (DMSO-$d_6$, 500 MHz) δ 10.58 (s, 1H), δ 7.95 (d, J=8.5 Hz, 2H) δ 7.86 (d, J=9.0 Hz, 2H), δ 7.65 (d, J=8.5 Hz, 2H), δ 7.52 (d, J=8.5 Hz, 2H); ¹³C NMR (DMSO-d₆, 125 MHz) δ 166.1, 163.8, 162.7, 139.8, 132.6, 131.9, 129.9, 129.5, 127.8, 120.1, 116.9, 93.2, 88.4, 52.8. Mass spectra (ESI): m/e 322 (M–H)⁻. HRMS (ESI-TOF, [M–H]⁻) m/z calcd for $C_{18}H_{12}NO_5$ 322.0715, found 322.0712.

2-((4-((4-hydroxy-3-(methoxycarbonyl)phenyl)ethynyl)phenyl)amino)-2-oxoacetic Acid (4b)

Pale yellow solid; (238 mg, 71% yield). ¹H NMR (DMSO-d₆, 500 MHz) δ 10.79 (s, 1H), δ 10.70 (s, 1H), 87.87 (d, J=2.0 Hz, 1H) 87.81 (d, J=7.0 Hz, 2H), δ 7.62 (d, J=8.5 Hz, 1H), δ 7.49 (d, J=9.0 Hz, 2H), δ 7.01 (d, J=8.5 Hz, 1H), 3.87 (s, 3H); ¹³C NMR (DMSO-d₆, 125 MHz) δ 168.4, 162.5, 160.1, 158.3, 138.6, 138.2, 133.7, 132.3, 120.5, 118.7, 118.3, 114.7, 113.8, 88.7, 88.4. Mass spectra (ESI): m/e 338 (M–H)⁻. HRMS (ESI-TOF, [M+H]⁺) m/z calcd for $C_{18}H_{14}NO_6$ 340.0815, found 340.0815.

2-((4-((3-hydroxy-4-(methoxycarbonyl)phenyl)ethynyl)phenyl)amino)-2-oxoacetic Acid (4c)

Pale yellow solid; (240 mg, 72% yield). ¹H NMR (DMSO-d₆, 500 MHz) δ 10.87 (s, 1H), δ 10.57 (s, 1H), δ 7.87 (br, 2H), δ 7.76 (d, J=8.5 Hz, 1H), δ 7.55 (d, J=6.5 Hz, 2H), δ 7.10 (s, 1H), δ 7.06 (d, J=8.5 Hz, 1H), δ 3.87 (s, 3H); ¹³C NMR (DMSO-d₆, 125 MHz) δ 168.8, 159.9, 132.8, 130.9, 129.5, 122.7, 120.6, 120.0, 117.6, 113.9, 92.7, 88.4, 53.0. Mass spectra (ESI): m/e 338 (M–H)⁻. HRMS (ESI-TOF, [M+H]⁺) m/z calcd for $C_{18}H_{14}NO_6$ 340.0815, found 340.0815.

2-((4-((2-(dimethylamino)-4-hydroxy-5-(methoxycarbonyl)phenyl)ethynyl)phenyl)amino)-2-oxoacetic Acid (4d)

Pale yellow solid; (264 mg, 70% yield). ¹H NMR (DMSO-d₆, 500 MHz) δ 10.71 (s, 1H), δ 7.85 (br, 1H), δ 7.78 (s, 1H), δ 7.59 (s, 1H), δ 7.48 (s, 1H), δ 6.29 (s, 1H), δ 3.84 (s, 3H), δ 3.08 (s, 6H); ¹³C NMR (DMSO-d₆, 125 MHz) δ 169.0, 161.9, 158.9, 137.2, 133.7, 131.7, 120.8, 119.3, 103.9, 103.5, 103.0, 92.7, 88.8, 52.6. Mass spectra (ESI): m/e 381 (M–H)⁻. HRMS (ESI-TOF, [M+H]⁺) m/z calcd for $C_{20}H_{19}N_2O_6$ 383.1237, found 383.1236.

2-((3-((2-(dimethylamino)-4-hydroxy-5-(methoxycarbonyl)phenyl)ethynyl)phenyl)amino)-2-oxoacetic Acid (4e)

White powder; (259 mg, 69% yield). ¹H NMR (DMSO-d₆, 500 MHz) δ 10.72 (s, 1H), δ 7.94 (s, 1H), δ 7.93 (s, 1H), δ 7.75 (d, J=8.5 Hz, 1H) 67.35 (t, J=8.0 Hz, 1H), 67.23 (d, J=10.0 Hz, 1H), 66.30 (s, 1H), δ 3.84 (s, 3H), δ 3.09 (s, 6H); ¹³C NMR (DMSO-d₆, 125 MHz) δ 168.9, 162.5, 162.1, 158.9, 158.2, 138.6, 137.4, 129.7, 126.9, 123.7, 122.4, 120.5, 104.0, 103.2, 103.0, 92.5, 89.2, 52.5; Mass spectra (ESI): m/e 381 (M–H)⁻. HRMS (ESI-TOF, [M+H]⁺) m/z calcd for $C_{20}H_{19}N_2O_6$ 383.1237, found 383.1236.

5-((4-(carboxyformamido)phenyl)ethynyl)-4-(dimethylamino)-2-hydroxybenzoic Acid (4f)

Off-white solid; (245 mg, 68% yield). ¹H NMR (DMSO-d₆, 500 MHz) δ 10.81 (s, 1H), δ 7.81 (d, J=7.5 Hz, 2H), δ 7.76 (s, 1H), δ 7.46 (d, J=8.0 Hz, 2H), δ 6.27 (s, 1H), δ 3.06 (s, 6H); ¹³C NMR (DMSO-d₆, 125 MHz) δ 171.6, 162.9, 159.0, 137.4, 133.6, 131.6, 120.7, 119.3, 104.7, 103.3, 103.0, 92.5, 89.1, 42.6; Mass spectra (ESI): m/e 367 (M–H)⁻. HRMS (ESI-TOF, [M+H]⁺) m/z calcd for $C_{19}H_{17}N_2O_6$ 369.1081, found 369.1081.

5-((3-(carboxyformamido)phenyl)ethynyl)-4-(dimethylamino)-2-hydroxybenzoic Acid (4g)

Off-white solid; (238 mg, 66% yield). ¹H NMR (DMSO-d₆, 500 MHz) δ 10.57 (s, 1H), δ 7.95 (s, 1H), δ 7.78 (s, 1H), δ 7.75 (d, J=7.5 Hz, 1H), δ 7.33 (t, J=7.5 Hz, 1H), δ 7.20 (d, J=7.5 Hz, 1H), δ 6.26 (s, 1H), δ 3.04 (s, 6H); ¹³C NMR (DMSO-d₆, 125 MHz) δ 171.7, 163.4, 158.9, 138.9, 137.4, 129.6, 126.6, 123.9, 122.2, 120.2, 106.4, 103.2, 102.8, 92.3, 89.7, 42.7. Mass spectra (ESI): m/e 367 (M–H)⁻. HRMS (ESI-TOF, [M+H]⁺) m/z calcd for $C_{18}H_{17}N_2O_6$ 369.1081, found 369.1081.

2-((4-((4-(tert-butyl)phenyl)ethynyl)phenyl)amino)-2-oxoacetic Acid (4h)

Pale yellow solid; (259 mg, 82% yield). ¹H NMR (DMSO-d₆, 500 MHz) δ 10.30 (s, 1H), δ 7.80 (d, J=9.0 Hz, 2H) δ 7.42 (q, J=9.0, 8.0 Hz, 6H), δ 1.27 (s, 9H); ¹³C NMR (DMSO-d₆, 125 MHz) δ 164.8, 162.7, 151.6, 139.9, 132.3, 131.5, 126.0, 120.1, 119.5, 116.9, 89.6, 88.9, 35.0, 31.4. Mass spectra (ESI): n/e 320 (M–H)⁻. HRMS (ESI-TOF, [M–H]⁻) m/z calcd for $C_{20}H_{18}NO_3$ 320.1281, found 320.1280.

2-oxo-2-((4-((4-(trifluoromethoxy)phenyl)ethynyl)phenyl)amino)acetic Acid (4l)

Pale-yellow powder; (268 mg, 78% yield). ¹H NMR (DMSO-d₆, 500 MHz) δ 10.69 (s, 1H), δ 7.83 (d, J=8.5 Hz, 2H) δ 7.65 (d, J=8.5 Hz, 2H), δ 7.51 (d, J=8.5 Hz, 2H), δ 7.40 (d, J=8.0 Hz, 2H); ¹³C NMR (DMSO-d₆, 125 MHz) δ 162.6, 159.9, 148.5, 139.4, 133.8, 132.5, 122.3, 121.84, 120.3, 117.4, 90.9, 87.8. Mass spectra (ESI): m/e 348 (M–H)⁻. HRMS (ESI-TOF, [M–H]⁻) m/z calcd for $C_{17}H_9F_3NO_4$ 348.0485, found 348.0482.

2-oxo-2-((4-((3-(trifluoromethyl)phenyl)ethynyl)phenyl)amino)acetic Acid (4j)

White solid; (267 mg, 81% yield). ¹H NMR (DMSO-d₆, 500 MHz) δ 10.89 (s, 1H), δ 7.82-7.87 (m, 4H) δ 7.74 (d, J=8.0 Hz, 1H), δ 7.64 (t, J=8.0 Hz, 1H), δ 7.56 (d, J=8.5 Hz, 2H); ¹³C NMR (DMSO-d₆, 125 MHz) δ 1162.4, 157.6, 139.0, 135.6, 132.7, 130.5, 130.2, 129.9, 129.7, 128.2, 125.6, 125.3, 124.0, 123.1, 120.7, 117.8, 91.4, 87.9. Mass spectra (ESI): m/e 332 (M–H)⁻. HRMS (ESI-TOF, [M–H]⁻) m/z calcd for $C_{17}H_9F_3NO_3$ 332.0534, found 332.0532.

2-oxo-2-((4-((4-(trifluoromethyl)phenyl)ethynyl)phenyl)amino)acetic Acid (4k)

Off-white solid; (263 mg, 80% yield). ¹H NMR (DMSO-d₆, 500 MHz) δ 10.91 (s, 1H), δ 7.85 (d, J=8.5 Hz, 2H) δ 7.75 (dd, J=15.0, 9.0 Hz, 4H), δ 7.57 (t, J=7.0 Hz, 2H); ¹³C NMR (DMSO-d₆, 125 MHz) δ 162.3, 157.5, 139.1, 132.7, 132.5, 129.3, 129.1, 128.8, 128.6, 127.2, 126.1, 125.5, 123.4, 120.7, 117.7, 92.3, 88.1. Mass spectra (ESI): m/e 332 (M–H)⁻. HRMS (ESI-TOF, [M–H]⁻) m/z calcd for $C_{17}H_9F_3NO_3$ 332.0534, found 332.0532.

2-oxo-2-((4-((4-sulfamoylphenyl)ethynyl)phenyl)amino)acetic Acid (4l)

Off-white solid; (226 mg, 67% yield). ¹H NMR (DMSO-d₆, 500 MHz) δ 10.79 (s, 1H), δ 7.82-7.86 (m, 2H) δ 7.71

(d, J=8.5 Hz, 1H), δ 7.53-7.62 (m, 3H), δ 7.45 (s, 1H); $^{13}$C NMR (DMSO-d$_6$, 125 MHz) δ 162.5, 159.0, 144.1, 139.4, 133.6, 132.7, 132.5, 132.2, 132.0, 131.9, 129.3, 129.2, 126.5, 126.3, 120.5, 117.4, 92.3, 88.3. Mass spectra (ESI): m/e 343 (M–H)$^-$ 367 (M+Na)$^+$. HRMS (ESI-TOF, [M–H]$^-$) m/z calcd for C$_{16}$H$_{12}$N$_2$O$_5$S 343.0388, found 343.0391.

2-((4-((4-hydroxyphenyl)ethynyl)phenyl)amino)-2-oxoacetic Acid (4m)

White solid; (230 mg, 83% yield). $^1$H NMR (DMSO-d$_6$, 500 MHz) δ 10.78 (s, 1H), δ 7.80 (d, J=8.5 Hz, 2H) δ 7.45 (d, J=8.5 Hz, 2H), δ 7.34 (d, J=8.5 Hz, 2H), δ 6.78 (d, J=8.5 Hz, 2H); $^{13}$C NMR (DMSO-d$_6$, 125 MHz) δ 162.5, 158.5, 158.1, 138.2, 133.4, 132.1, 120.56, 119.0, 116.2, 113.0, 90.1, 87.7; Mass spectra (ESI): m/e 280 (M–H)$^-$. HRMS (ESI-TOF, [M+H]$^+$) m/z calcd for C$_{16}$H$_{12}$NO$_4$ 282.0761, found 282.0759.

2-((4-((3-bromo-4-hydroxyphenyl)ethynyl)phenyl)amino)-2-oxoacetic Acid (4n)

Pale yellow powder; (261 mg, 74% yield). $^1$H NMR (DMSO-d$_6$, 500 MHz) δ 10.83 (s, 1H), δ 7.81 (d, J=8.5 Hz, 2H) δ 7.64 (d, J=2.0 Hz, 1H), δ 7.47 (d, J=8.5 Hz, 2H), δ 7.35 (dd, J=8.5, 2.0 Hz, 1H), δ 6.96 (d, J=8.5 Hz, 1H); $^{13}$C NMR (DMSO-d$_6$, 125 MHz) δ 162.5, 157.7, 155.3, 138.4, 136.0, 132.5, 132.2, 120.6, 118.6, 116.9, 114.7, 109.7, 88.7, 88.4; Mass spectra (ESI): m/e 358 (M–H)$^-$. HRMS (ESI-TOF, [M–H]$^-$) m/z calcd for C$_{16}$H$_9$NO$_4$ 357.9715, found 357.9727.

2-((4-((4-cyanophenyl)ethynyl)phenyl)amino)-2-oxoacetic Acid (4o)

White powder; (226 mg, 79% yield). $^1$H NMR (DMSO-d$_6$, 500 MHz) δ 10.92 (s, 1H), δ 7.86 (d, J=8.5 Hz, 4H), δ 7.70 (d, J=8.5 Hz, 2H), δ 7.57 (d, J=8.0 Hz, 2H); $^{13}$C NMR (DMSO-d$_6$, 125 MHz) δ 162.5, 157.5, 139.3, 133.1, 132.8, 132.5, 127.8, 120.7, 118.9, 117.6, 111.3, 93.9, 88.2. Mass spectra (ESI): m/e 289 (M–H)$^-$. HRMS (ESI-TOF, [M+H]$^+$) m/z calcd for C$_{17}$H$_{11}$N$_2$O$_3$ 291.0764, found 291.0764.

2-((4-((3,5-bis(trifluoromethyl)phenyl)ethynyl)phenyl)amino)-2-oxoacetic Acid (4p)

Off-white solid; (305 mg, 77% yield). $^1$H NMR (DMSO-d$_6$, 500 MHz) δ 10.53 (s, 1H), δ 8.22 (s, 2H) δ 8.09 (s, 1H), δ 7.87 (d, J=8.5 Hz, 2H), δ 7.55 (d, J=8.5 Hz, 2H); $^{13}$C NMR (DMSO-d$_6$, 125 MHz) δ 162.8, 162.7, 140.4, 132.8, 132.2, 131.7, 131.4, 131.2, 130.9, 125.8, 124.5, 122.3, 122.1, 119.9, 116.0, 93.7, 86.3. Mass spectra (ESI): m/e 400 (M–H)$^-$. HRMS (ESI-TOF, [M–H]$^-$) m/z calcd for C$_{18}$H$_8$F$_6$NO$_3$ 400.0408, found 400.0413.

2-((4-(naphthalen-2-ylethynyl)phenyl)amino)-2-oxoacetic Acid (4q)

Off-white solid; (249 mg, 80% yield). $^1$H NMR (DMSO-d$_6$, 500 MHz) δ 10.70 (s, 1H), δ 8.15 (s, 1H), δ 7.92-7.95 (m, 3H), δ 7.85 (d, J=8.5 Hz, 2H), δ 7.54-7.59 (m, 5H); $^{13}$C NMR (DMSO-d$_6$, 125 MHz) δ 162.5, 139.3, 133.1, 132.8, 132.5, 131.5, 128.8, 128.5, 128.2, 127.3, 120.3, 117.8, 90.3, 89.6. Mass spectra (ESI): m/e 314 (M–H)$^-$. HRMS (ESI-TOF, [M–H]$^-$) m/z calcd for C$_{20}$H$_{12}$NO$_3$ 314.0811, found 314.0812.

2-((4-((4-(benzyloxy)phenyl)ethynyl)phenyl)amino)-2-oxoacetic Acid (4r)

White powder; (245 mg, 67% yield). $^1$H NMR (DMSO-d$_6$, 500 MHz) δ 10.69 (s, 1H), δ 7.84 (br, 2H), δ 7.55 (d, J=8.0 Hz, 2H), δ 7.43-7.47 (m, 5H), δ 7.38 (t, J=8.5 Hz, 2H), δ 7.33 (t, J=7.5 Hz, 2H), δ 7.03 (d, J=8.5 Hz, 2H), δ 5.12 (s, 2H); $^{13}$C NMR (DMSO-d$_6$, 125 MHz) δ 159.0, 137.2, 133.6, 133.3, 132.2, 128.9, 128.4, 128.3, 120.4, 118.4, 115.7, 115.1, 89.4, 88.6, 69.8. Mass spectra (ESI): m/e 370 (M–H)$^-$. HRMS (ESI-TOF, [M–H]$^-$) m/z calcd for C$_{23}$H$_{16}$NO$_4$ 370.1076, found 370.1076.

2-((4-((4-((tert-butoxycarbonyl)amino)phenyl)ethynyl)phenyl)amino)-2-oxoacetic Acid (4s)

Pale yellow solid; (275 mg, 73% yield). $^1$H NMR (DMSO-d$_6$, 500 MHz) δ 10.80 (s, 1H), δ 9.57 (s, 1H), δ 7.81 (d, J=8.5 Hz, 2H) δ 7.40-7.50 (m, 6H), δ 1.46 (s, 2H); $^{13}$C NMR (DMSO-d$_6$, 125 MHz) δ 162.5, 158.2, 153.0, 140.5, 138.4, 132.3, 132.2, 120.6, 118.7, 118.4, 115.9, 89.8, 88.6, 79.9, 28.5. Mass spectra (ESI): m/e 379 (M–H)$^-$. HRMS (ESI-TOF, [M–H]$^-$) m/z calcd for C$_{21}$H$_{19}$N$_2$O$_5$ 379.1294, found 379.1300.

2-((4-((2-chloro-4-(trifluoromethyl)phenyl)ethynyl)phenyl)amino)-2-oxoacetic Acid (4t)

Off-white powder; (280 mg, 77% yield). $^1$H NMR (DMSO-d$_6$, 500 MHz) δ 10.78 (s, 1H), δ 8.00 (s, 1H), δ 7.87 (t, J=9.0 Hz, 3H) δ 7.74 (d, J=8.5 Hz, 1H), δ 7.57 (d, J=8.5 Hz, 2H); $^{13}$C NMR (DMSO-d$_6$, 125 MHz) δ 162.5, 159.6, 139.9, 135.7, 134.5, 132.8, 130.3, 130.1, 126.9, 126.7, 124.7, 122.5, 120.4, 116.7, 97.7, 84.9. Mass spectra (ESI): m/e 366 (M–H)$^-$. HRMS (ESI-TOF, [M–H]$^-$) m/z calcd for C$_{17}$H$_7$ClF$_3$NO$_3$ 366.0145, found 366.0143.

2-((4-((2-bromo-4-(trifluoromethyl)phenyl)ethynyl)phenyl)amino)-2-oxoacetic Acid (4u)

Off-white powder; (302 mg, 74% yield). $^1$H NMR (DMSO-d$_6$, 500 MHz) δ 10.65 (s, 1H), δ 8.12 (s, 1H), δ 7.82-7.88 (m, 3H), δ 7.78 (d, J=8.5 Hz, 1H), δ 7.56 (d, J=8.5 Hz, 2H); $^{13}$C NMR (DMSO-d$_6$, 125 MHz) δ 162.6, 161.0, 140.2, 134.3, 132.8, 129.6, 129.2, 125.6, 125.1, 120.2, 116.4, 97.2, 86.9. Mass spectra (ESI): m/e 410 (M–H)$^-$. HRMS (ESI-TOF, [M–H]$^-$) m/z calcd for C$_{17}$H$_8$BrF$_3$NO$_3$ 409.9640, found 409.9636.

2-((4-((2-fluoro-4-(trifluoromethyl)phenyl)ethynyl)phenyl)amino)-2-oxoacetic Acid (4v)

White solid; (292 mg, 84% yield). $^1$H NMR (DMSO-d$_6$, 500 MHz) δ 10.76 (s, 1H), δ 7.87 (d, J=9.0 Hz, 2H) δ 7.79 (t, J=8.0 Hz, 1H), 67.70 (d, J=11.5 Hz, 1H), 67.55 (d, J=8.5 Hz, 3H); $^{13}$C NMR (DMSO-d$_6$, 125 MHz) δ 162.6, 160.2, 159.7, 158.1, 139.8, 132.8, 129.8, 129.7, 128.4, 128.2, 123.9, 121.8, 120.4, 120.0, 119.8, 116.7, 93.8, 86.9. Mass spectra (ESI): m/e 350 (M–H)$^-$. HRMS (ESI-TOF, [M–H]$^-$) m/z calcd for C$_{17}$H$_8$F$_4$NO$_3$ 350.0435, found 350.0442.

2-((4-((2-cyano-4-(trifluoromethyl)phenyl)ethynyl)phenyl)amino)-2-oxoacetic Acid (4w)

Pale yellow solid; (250 mg, 71% yield). $^1$H NMR (DMSO-d$_6$, 500 MHz) δ 10.78 (s, 1H), δ 8.41 (s, 1H) δ 8.07 (d, J=8.5 Hz, 1H), δ 7.94 (d, J=11.5 Hz, 1H), δ 7.90 (d, J=8.5

Hz, 2H), δ 7.58 (d, J=8.5 Hz, 2H); $^{13}$C NMR (DMSO-$d_6$, 125 MHz) δ 162.6, 160.1, 140.4, 133.4, 133.1, 130.7, 130.4, 129.8, 129.5, 129.3, 129.0, 124.5, 122.4, 120.5, 116.8, 115.9, 115.4, 98.7, 85.0; Mass spectra (ESI): m/e 357 (M–H)$^-$. HRMS (ESI-TOF, [M–H]$^-$) m/z calcd for $C_{18}H_8F_3N_2O_3$ 357.0487 found 357.0493.

2-((4-((2,4-bis(trifluoromethyl)phenyl)ethynyl)phenyl)amino)-2-oxoacetic Acid (4x)

White powder; (275 mg, 73% yield). $^1$H NMR (DMSO-$d_6$, 500 MHz) δ 10.87 (s, 1H), δ 8.10 (s, 2H), δ 8.01 (d, J=8.5 Hz, 1H), δ 7.88 (d, J=8.5 Hz, 2H), δ 7.55 (d, J=8.5 Hz, 2H); $^{13}$C NMR (DMSO-$d_6$, 125 MHz) δ 162.4, 158.6, 139.9, 135.4, 132.8, 130.1, 125.2, 123.6, 120.7, 116.7, 98.3, 84.2; Mass spectra (ESI): m/e 400 (M–H)$^-$. HRMS (ESI-TOF, [M–H]$^-$) m/z calcd for $C_{18}H_8F_6NO_3$ 400.0408, found 400.0415.

2-oxo-2-((3-(phenylethynyl)phenyl)amino)acetic Acid (5)

Off-White solid; (229 mg, 88% yield). $^1$H NMR (DMSO-$d_6$, 500 MHz) δ 10.73 (s, 1H), δ 8.00 (s, 1H), δ 7.74-7.77 (m, 1H) δ 7.54.7.56 (m, 2H), δ 7.39-7.43 (d, 3H), δ 7.37 (d, J=7.5 Hz, 2H), δ 7.29 (d, J=7.5 Hz, 1H); $^{13}$C NMR (DMSO-$d_6$, 125 MHz) δ 162.6, 158.6, 138.7, 131.9, 129.7, 129.4, 129.3, 127.7, 122.9, 122.6, 121.1, 89.7, 89.6. Mass spectra (ESI): m/e 264 (M–H)$^-$. HRMS (ESI-TOF, [M–H]$^-$) m/z calcd for $C_{16}H_{10}NO_3$ 264.0661, found 264.0670.

Synthesis of 2-([1,1'-biphenyl]-4-ylamino)-2-oxoacetic Acid (6)

To a stirred solution of 4-biphenylamine (300 mg, 1.77 mmol) and N,N-diisopropyl ethylamine (613 μL, 3.55 mmol) in 20 mL of anhydrous $CH_2Cl_2$ was added methyl chlorooxoacetate (180 μL, 1.95 mmol) drop-wise under $N_2$ atmosphere. The resulting solution was stirred at room temperature for 30 min. The reaction mixture was washed with 20 mL of DI water and 20 mL of brine. The organic layer was dried over anhydrous $Na_2SO_4$ and evaporated in vacuo. Crude ester subjected for hydrolysis using 15 mL of 1N KOH/THF (1:1 v/v) at room temperature for 1 hour. After completion, THF evaporated and aqueous layer acidified to pH~2 using 3N HCL and resulting solid filtered. Products were then purified by column chromatography on silica gel eluted with a mixture of methanol-dichloromethane. White solid; (374 mg, 87% yield). $^1$H NMR (DMSO-$d_6$, 500 MHz) δ 10.80 (s, 1H), δ 7.86 (d, J=8.5 Hz, 2H), δ 7.63-7.66 (m, 4H), δ 7.43 (t, J=7.5 Hz, 2H), δ 7.32 (t, J=7.5 Hz, 1H); $^{13}$C NMR (DMSO-$d_6$, 125 MHz) δ 162.6, 157.4, 139.9, 137.6, 136.6, 129.4, 127.7, 127.4, 126.8, 121.1. Mass spectra (ESI): m/e 240 (M–H)$^-$. HRMS (ESI-TOF, [M–H]$^-$) m/z calcd for $C_{14}H_{10}NO_3$ 240.0661, found 240.0669.

Synthesis of 2-([1,1'-biphenyl]-3-ylamino)-2-oxoacetic Acid (7)

To an ice-cold solution of 3-biphenylamine (300 mg, 1.77 mmol) and N,N-diisopropyl ethylamine (613 μL, 3.55 mmol) in 20 mL of anhydrous $CH_2Cl_2$ was added methyl chlorooxoacetate (180 μL, 1.95 mmol) drop-wise under $N_2$ atmosphere. The resulting solution was stirred at room temperature for 30 min. The reaction mixture was washed with 20 mL of DI water and 20 mL of brine. The organic layer was dried over anhydrous $Na_2SO_4$ and evaporated in vacuo. Crude ester subjected for hydrolysis using 15 mL of 1N KOH/THF (1:1 v/v) at room temperature for 1 hour. After completion, THF evaporated and aqueous layer acidified to pH~2 using 3N HCL and resulting solid filtered. Products were then purified by column chromatography on silica gel eluted with a mixture of methanol-dichloromethane. White powder; (360 mg, 84% yield). $^1$H NMR (DMSO-$d_6$, 500 MHz) δ 10.75 (s, 1H), δ 8.08 (s, 1H), δ 7.78 (dt, J=7.0, 2.0 Hz, 2H), δ 7.61 (d, J=9.5 Hz, 1H), δ 7.41-7.48 (m, 4H), δ 7.36 (t, J=7.0 Hz, 1H); $^{13}$C NMR (DMSO-$d_6$, 125 MHz) δ 162.6, 157.7, 141.2, 140.4, 138.8, 129.8, 129.5, 128.1, 127.1, 123.3, 119.7, 119.1. Mass spectra (ESI): m/e 240 (M–H)$^-$. HRMS (ESI-TOF, [M–H]$^-$) m/z calcd for $C_{14}H_{10}NO_3$ 240.0661, found 240.0669.

Synthesis of 2-oxo-2-(quinolin-3-ylamino)acetic Acid (8)

To a stirred solution of 3-aminoquinoline (400 mg, 2.77 mmol) and N,N-diisopropyl ethylamine (960 μL, 5.55 mmol) in 25 mL of anhydrous $CH_2Cl_2$ was added methyl chlorooxoacetate (281 μL, 3.05 mmol) drop-wise under $N_2$ atmosphere. The resulting solution was stirred at room temperature for 30 min. The reaction mixture was washed with 25 mL of DI water and 25 mL of brine. The organic layer was dried over anhydrous $Na_2SO_4$ and evaporated in vacuo. Crude ester subjected for hydrolysis using 20 mL of 1N KOH/THF (1:1 v/v) at room temperature for 1 hour. After completion, THF evaporated and aqueous layer acidified to pH~2 using 3N HCL and resulting solid filtered. Compound 7 was then purified by column chromatography on silica gel eluted with a mixture of methanol-dichloromethane. Yellow powder; (450 mg, 75% yield). $^1$H NMR (DMSO-$d_6$, 500 MHz) δ 11.35 (s, 1H), δ 9.25 (s, 1H), δ 8.97 (s, 1H), δ 8.07 (t, J=7.0 Hz, 2H), δ 7.78 (t, J=7.0 Hz, 1H), δ 7.67 (t, J=7.0 Hz, 1H); $^{13}$C NMR (DMSO-$d_6$, 125 MHz) δ 161.9, 158.0, 143.8, 142.2, 132.3, 130.4, 128.7, 128.5, 128.2, 127.1, 126.7. Mass spectra (ESI): m/e 215 (M–H)$^-$. HRMS (ESI-TOF, [M–H]$^-$) m/z calcd for $C_{11}H_7N_2O_3$ 215.0457, found 215.0464.

(Z)-2-oxo-2-((4-styrylphenyl)amino)acetic Acid (9)

Off-white powder; (37 mg, 74% yield). $^1$H NMR (DMSO-$d_6$, 500 MHz) δ 10.67 (s, 1H), δ 7.64 (d, 8.5 Hz, 2H), δ 7.24 (d, 8.5 Hz, 2H), δ 7.19-7.22 (m, 3H), δ 7.16 (d, J=8.5 Hz, 1H), δ 6.57 (s, 2H); $^{13}$C NMR (DMSO-$d_6$, 125 MHz) δ 162.6, 157.9, 137.4, 137.3, 133.3, 130.1, 129.9, 129.4, 129.0, 128.9, 128.8, 128.7, 127.7, 120.4. Mass spectra (ESI): m/e 266 (M–H)$^-$. HRMS (ESI-TOF, [M–H]$^-$) m/z calcd for $C_{17}H_{12}NO_3$ 266.0817, found 266.0826.

(Z)-2-oxo-2-((4-(4-(trifluoromethyl)styryl)phenyl)amino)acetic Acid (10)

Off-white powder; (32 mg, 72% yield). $^1$H NMR (DMSO-$d_6$, 500 MHz) δ 10.71 (s, 1H), δ 7.68 (d, J=8.0 Hz, 2H), 67.61 (d, J=8.0 Hz, 2H), δ 7.41 (d, J=8.5 Hz, 2H), δ 7.17 (d, J=8.5 Hz, 2H), δ 6.72 (d, J=12 Hz, 1H), δ 7.64 (d, J=12 Hz, 1H); $^{13}$C NMR (DMSO-$d_6$, 125 MHz) δ 162.5, 157.8, 141.7, 137.6, 132.7, 132.1, 129.7, 129.5, 128.6, 125.8, 120.5. Mass spectra (ESI): m/e 334 (M–H)$^-$. HRMS (ESI-TOF, [M–H]$^-$) m/z calcd for $C_{17}H_{11}F_3NO_3$ 334.0691, found 334.0702.

2-oxo-2-((4-phenethylphenyl)amino)acetic Acid (11)

White crystals; (47 mg, 93% yield). $^1$H NMR (MeOH-$d_4$, 500 MHz) δ 7.56 (d, J=8.5 Hz, 2H), δ 7.21-7.24 (m, 2H), δ

7.12-7.16 (m, 5H), δ 2.88 (s, 4H); $^{13}$C NMR (MeOH-d$_4$, 125 MHz) δ 141.5, 138.2, 135.0, 128.5, 128.2, 127.9, 125.5, 119.8, 37.6, 37.2. Mass spectra (ESI): m/e 268 (M–H)$^-$. HRMS (ESI-TOF, [M–H]$^-$) m/z calcd for $C_{16}H_{15}NO_3$ 268.0968, found 268.0980.

2-oxo-2-((4-(4-(trifluoromethyl)phenethyl)phenyl) amino)acetic Acid (12)

White crystals; (45 mg, 90% yield). $^1$H NMR (DMSO-d$_6$, 500 MHz) δ 10.61 (s, 1H), δ 7.59-7.64 (m, 4H) δ 7.42 (d, J=8.0 Hz, 2H), δ 7.18 (d, J=8.5 Hz, 2H), δ 2.93-2.96 (m, 2H), δ 2.84-2.88 (m, 2H); $^{13}$C NMR (DMSO-d$_6$, 125 MHz) δ 162.6, 157.2, 146.9, 137.7, 136.1, 129.7, 129.1, 127.5, 127.2, 126.9, 126.7, 126.0, 125.5, 125.4, 123.8, 120.7, 37.0, 36.4. Mass spectra (ESI): m/e 336 (M–H)$^-$. HRMS (ESI-TOF, [M–H]$^-$) m/z calcd for $C_{17}H_{14}F3NO_3$ 336.0848, found 336.0852.

Molecular Modeling Studies.

The molecular modeling studies were performed using the previously published crystal structure of mPTPB in complex with OMTS (PDB code:20Z5). Schrodinger Molecular Modeling Suite 2019-4 (Schrodinger, LLC, New York, N.Y., 2019) was used for the modeling studies with procedures similar to those described before. Extra precision Glide (Glide-XP) was used for docking studies. Briefly, the structures of the protein-ligand complexes were prepared using the Protein Preparation module, and the ligand binding sites were defined based on the native ligand (OMTS). The inhibitors described in this study were built and prepared for docking using the Ligprep module. Data analyses were performed using the Maestro interface of the software.

Determination of Log D.

To determine the lipophilicity of our inhibitors, the Log D at pH 7.4 was measured using the shake flask method. An aliquot of 10 mM DMSO stock solutions of test compounds were added into an Eppendorf containing 2 mL of n-octanol and pH=7.4 phosphate buffered saline (1:1 v/v) to give a final concentration of 100 μM. The tubes were shaken for 8 hours, centrifuged at 10000 rpm for 5 minutes then n-octanol and phosphate buffered saline layers separated. Both layers were analyzed using LC-MS (Agilent Technologies 6470 series, triple quadrupole LC/MS). The ratios of AUC of the peaks were used to calculate the Log D in accordance with the equation:

Log $D$=Log$_{10}$(AUC of octanol layer/AUC of phosphate buffered saline layer)

Determination of Kinetic Solubility.

The kinetic solubility of compounds (4b, 4h, 4k, 4t, 4u, and 4v) was measured by diluting a 10 μL of 20 mM DMSO stock into 990 μL of PBS buffer at pH=7.4 (200 μM final inhibitor concentration) in a glass vial at 25° C. The resulting mixture was stirred at 500 rpm for 90 minutes and then filtered using 0.45 μm PVDF membrane filter. After filtration, the concentration of corresponding compound was determined by HPLC, comparing the AUC obtained with that from a standard solution of the compound. Data represent the mean (t standard deviation, SD) of three separate experiments, performed in triplicate.

Mouse Liver Microsomal Assays.

Mouse (CD-1) pooled liver microsomes purchased from Fisher Scientific, IL, USA (0.5 mg/mL, Corning Gentest 3P, cat#452702), and the assay procedures were followed as previously reported. A solution of mouse liver microsomes and 1 mM of co-factor NADPH in 1 ml of phosphate buffer saline (pH=7.4) was prewarmed to 37° C. in an Eppendorf tube. Then 10 μL of a test solution (10 mM DMSO stock) was added to initiate the reaction. Verapamil-HCl was used as a positive control. Another set of control inactive microsome experiments (without co-factor NADPH) were performed. The incubation mixture was kept at 37° C., and 50 μL aliquots were taken at times of 0, 5, 10, 15, 30 or 60 min. Each of the aliquot was quenched using 200 μL of ice-cold acetonitrile. The mixtures were vigorously vortexed and centrifuged to remove the precipitated protein and the supernatants were analyzed by an Agilent Technologies 6470 series, triple quadrupole LC/MS spectrometer to quantitate the remaining parent compound. The percent of the parent compound remaining was calculated from the formula:

% parent compound remaining=(concentration at 60 min/concentration at 0 min)*100

$IC_{50}$ Determination and $K_i$ Determination.

Compounds were tested against mPTPB using the p-nitrophenyl phosphate (pNPP) assay system in a Cary 100 UV-Vis spectrophotometer by monitoring the increase in absorbance of product formed, p-nitrophenol (pNP) at 405 nm. The reaction was started by the addition of mPTPB into a final volume of 200 μL master mix containing pH 7.0 3,3-Dimethyl glutarate buffer (50.0 mM, 1 mM EDTA, 0.15M NaCl), 3.0 mM pNPP. $IC_{50}$ values for each compound were determined by varying the concentration of the inhibitor at fixed concentrations of the enzyme and by fitting the dose-response data into the four-parameter logistic curve (eq 1) model of GraphPad prism 7.02, as follows.

$A_I/A_0=IC_{50}/(IC_{50}+[I])$ where $A_I$ is the absorbance at 405 nm of the sample with inhibitor; $A_0$ is the absorbance at 405 nm without inhibitor; and [I] is the concentration of the inhibitor.

For selectivity studies, the catalytic domain of PTPs, including SHP2, SHP1, PTP1B, mPTPA, TCPTP, FAP1, LAR, CD45-D1D2, PTPγ-D1D2, VHR, Cdc14A, LYP, PTP-MEG2, HePTP, PTPα-D1D2, Laforin, DEP-1-D1, MKP3, MKP5, YopH, PTP-PEST, STEP, PTPσ-D1D2, PTPβ-D1, PTPμ-D1, PTPε and LMWPTP were expressed and purified from E. coli (BL21). The inhibition assay for these PTPs were performed under the same conditions as mPTPB except using a different pNPP concentration corresponding to the $K_m$ of the FTP studied.

The inhibition constants ($K_i$) for the inhibitors against mPTPB were determined at pH 7.0 and 25° C. At various fixed concentrations of inhibitor, the initial rate for a series of pNPP concentrations was measured by following the production of p-nitrophenol (UV absorbance at 405 nm) as describe above, ranging from 0.2- to 5-fold the apparent $K_m$ values. The data were fitted using SigmaPlot-Enzyme Kinetics to obtain the inhibition constant and to assess the mode of inhibition.

Cell Permeability Studies.

The intracellular concentrations of novel compounds were determined in Raw264.7 cells using the previously reported protocol by Teuscher et al. See Teuscher, K. B.; Zhang, M.; Ji, H., A Versatile Method to Determine the Cellular Bioavailability of Small-Molecule Inhibitors. *J Med Chem* 2017, 60 (1), 157-169. The calibration curves of compounds are shown in supplementary figures S48 to S50. The results of the HPLC analyses are shown in supplementary figures S50 to S53. The input concentration was set to 20 μM. The cell-bound concentration of 4k, 4s, 4t and 4u at 37° C. was determined after 2h incubation in Dulbecco's modified Eagle's medium (DMEM) media with 10% FBS (Invitrogen), penicillin (50 units/mL), and streptomycin (50 µg/mL) respectively. In these experiments compound 9 was used as a positive control. All these compounds showed better cellular permeability compared to compound 9 under identical conditions.

Cell Culture and Transfection.

Raw264.7 mouse macrophages were cultured in Dulbecco's modified Eagle's medium (DMEM) supplemented with 10% FBS (Invitrogen), penicillin (50 units/mL), and streptomycin (50 µg/mL) under a humidified atmosphere containing 5% $CO_2$ at 37° C. Transfected Raw264.7 cells (Vector, WT-mPTPB) as previously reported were seeded in a 24-well plate at a density of $2\times10^4$ cells/well. See He, R.; Yu, Z.-H.; Zhang, R.-Y.; Wu, L.; Gunawan, A. M.; Zhang, Z.-Y., Cefsulodin Inspired Potent and Selective Inhibitors of mPTPB, a Virulent Phosphatase from *Mycobacterium tuberculosis*. *ACS Medicinal Chemistry Letters* 2015, 6 (12), 1231-1235. After 48 hours, the cells were treated with mPTPB inhibitor 4t at different concentrations for 2h and then stimulated with IFN-γ (20 ng/ml) for 1 h (compound 9 as our positive control). Cells were then washed with ice-cold phosphate buffered saline, and lysed with lysis buffer on ice for 30 min. Cell lysates were cleared by centrifugation at 13000 rpm for 15 min. The phosphorylation of ERK1/2, p38, and Akt was detected by Western blotting.

In one embodiment, the present disclosure provides a compound of formula I:

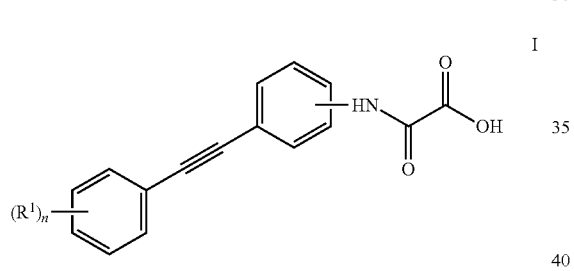

or a stereoisomer, tautomer, solvate, pharmaceutically acceptable salt thereof, wherein:

$(R^1)_n$ represents 1-3 independent $R^1$ being attached to the phenyl ring, wherein n is 1-3, wherein each of said 1-3 $R^1$ independently represents a H, F, Cl, Br, I, —CN, —$OR^2$, —$COOR^3$, —$NR^4R^5$, —CO—$R^6$, —$SO_2NR^7R^8$, an optionally substituted $C_1$-$C_8$ branched or unbranched alkyl chain, an optionally substituted $C_3$-$C_8$ cyclic alkyl, an optionally substituted aryl, or an optionally substituted heteroaryl comprising one or more O, N, or S, or when n is 2, two independent $R^1$ can join together to form a fused bicyclic ring with the phenyl ring; and $R^2$-$R^8$ each independently represents a H, an optionally substituted $C_1$-$C_8$ branched or unbranched alkyl chain, an optionally substituted $C_3$-$C_8$ cyclic alkyl, an optionally substituted aryl, or an optionally substituted heteroaryl comprising one or more O, N, or S, or a nitrogen protecting group.

In one embodiment of the present disclosure regarding the compound of formula I, wherein —HN—C(O)—COOH is on the para position of the directly attached phenyl group.

In one embodiment of the present disclosure regarding the compound of formula I, wherein one or more hydrogen on $R^1$-$R^8$ can be optionally substituted by one or more —OH, —F, —Cl, —Br, —CN, or $C_1$-$C_4$ alkoxy, or an optionally substituted phenyl group.

In one embodiment of the present disclosure regarding the compound of formula I, wherein each of said 1-3 $R^1$ independently represents a H, F, Cl, Br, I, —CN, —$CF_3$, —OH, —$OCF_3$, —$COCF_3$, —$COOCH_3$, —COOH, —$N(CH_3)_2$, —NHBoc, —$SO_2NH_2$, —$OCH_2Ph$, or two $R^1$ groups jointly form a ring to make a naphthalene ring with the phenyl group that the $R^1$ is directly attached.

In one embodiment of the present disclosure regarding the compound of formula I, wherein the compound is selected from the group consisting of:

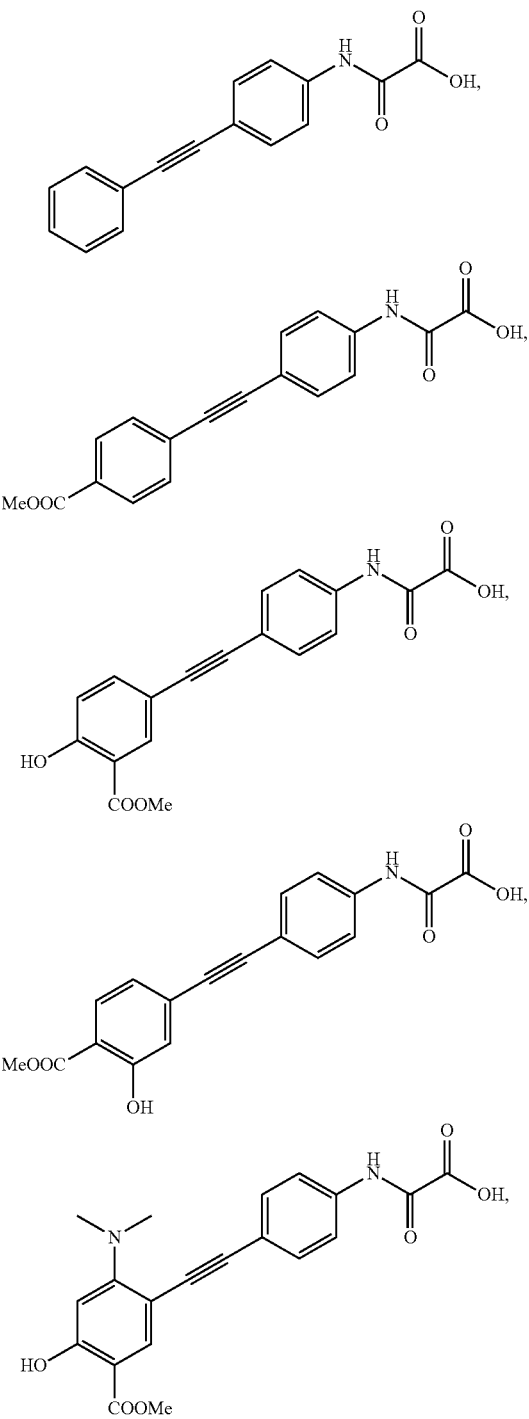

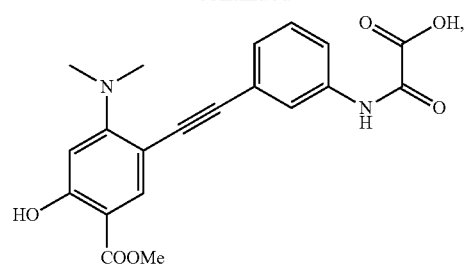
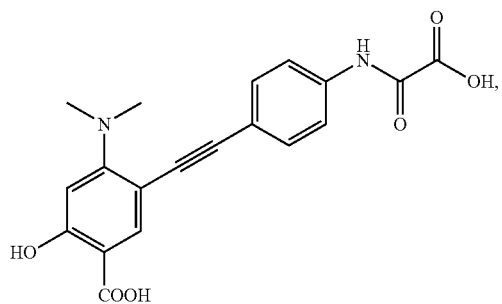
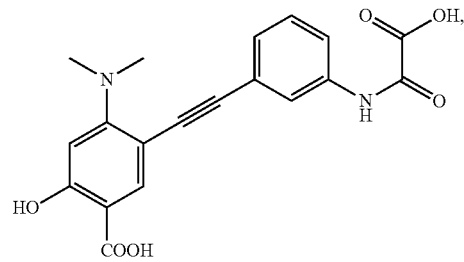
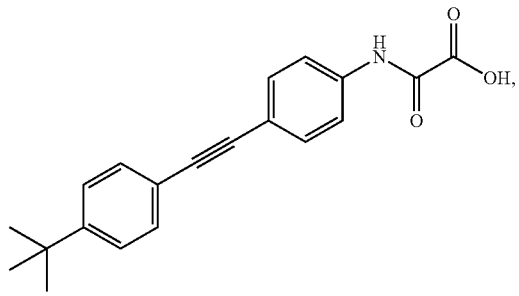
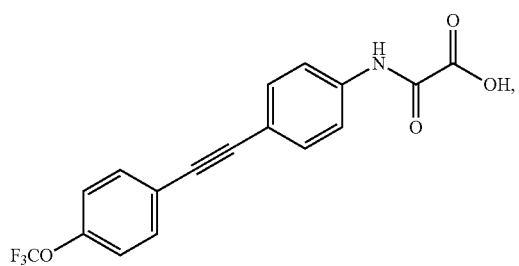
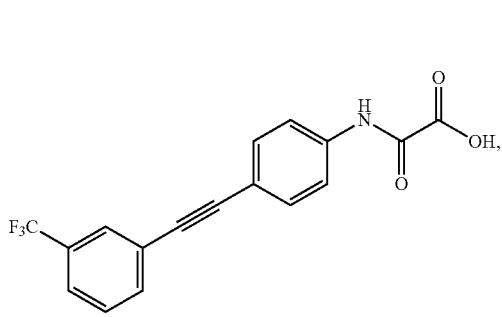
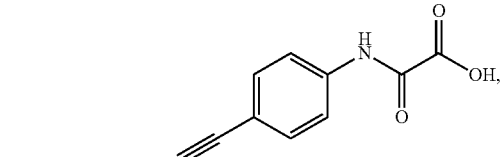
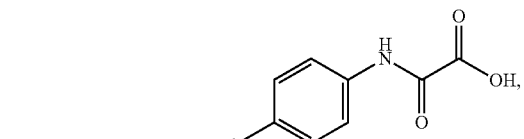
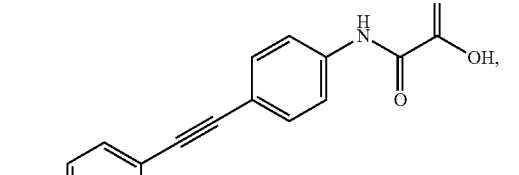
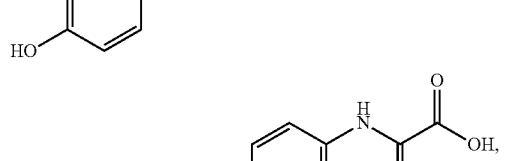
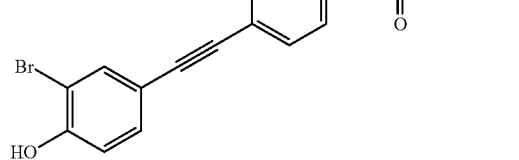
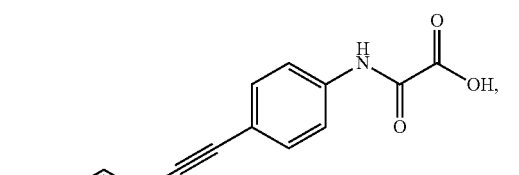
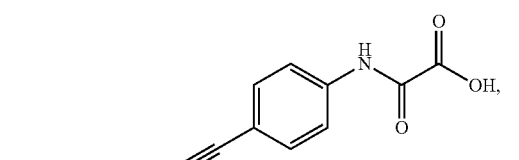

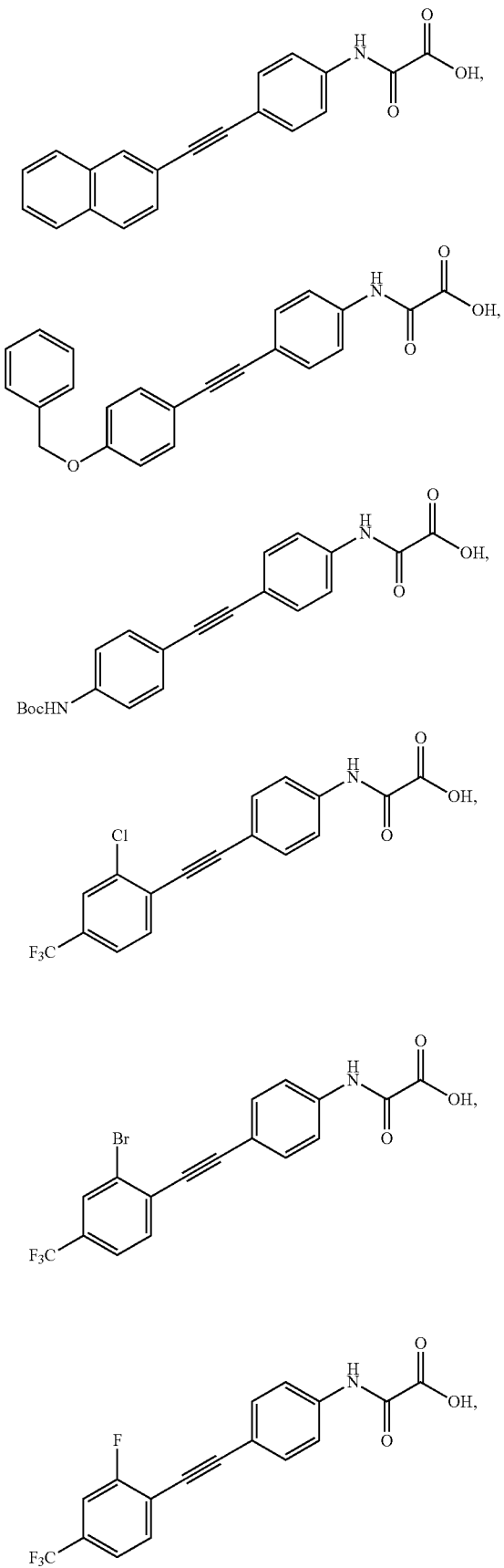

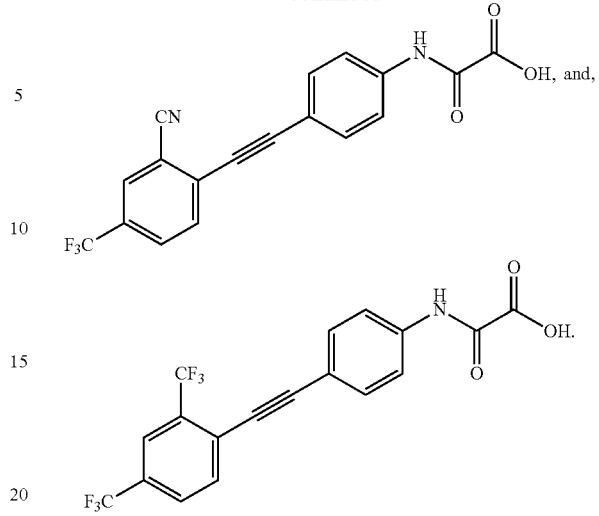

In one embodiment, the present disclosure provides a method of treating a patient having a Tuberculosis disease with a compound of formula I, or a stereoisomer, tautomer, solvate, pharmaceutically acceptable salt thereof.

In one embodiment of the present disclosure regarding the method of treating a patient having a Tuberculosis disease, wherein the compound of formula I inhibits *Mycobacterium tuberculosis* protein tyrosine phosphatase B (mPTPB).

Those skilled in the art will recognize that numerous modifications can be made to the specific implementations described above. The implementations should not be limited to the particular limitations described. Other implementations may be possible.

We claim:
1. A compound of formula I:

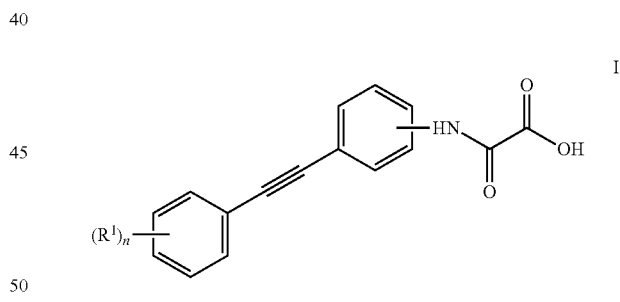

or a stereoisomer, tautomer, solvate, pharmaceutically acceptable salt thereof, wherein:

$(R^1)_n$ represents 1-3 independent $R^1$ being attached to the phenyl ring wherein n is 1-3, wherein each of said 1-3 $R^1$ independently represents a H, F, Cl, Br, I, —CN, —$OR^2$, —$COOR^3$, —$NR^4R^5$, —CO—$R^6$, —$SO_2NR^7R^8$, an optionally substituted $C_1$-$C_5$ branched or unbranched alkyl chain, an optionally substituted $C_3$-$C_8$ cyclic alkyl, an optionally substituted aryl, or an optionally substituted heteroaryl comprising one or more O, N, or S, or when n is 2, two independent $R^1$ can join together to form a fused bicyclic ring with the phenyl ring; and $R^2$-$R^8$ each independently represents a H, an optionally substituted $C_1$-$C_8$ branched or unbranched alkyl chain, an optionally substituted $C_3$-$C_8$ cyclic alkyl, an optionally substituted aryl, or an optionally substituted heteroaryl comprising one or more O, N, or S, or a nitrogen protecting group.

2. The compound of claim 1, wherein —HN—C(O)—COOH is on the para position of the directly attached phenyl group.

3. The compound of claim 1, wherein one or more hydrogen on $R^1$-$R^8$ can be optionally substituted by one or more —OH, —F, —Cl, —Br, —CN, or $C_1$-$C_4$ alkoxy, or an optionally substituted phenyl group.

4. The compound of claim 1, wherein each of said 1-3 $R^1$ independently represents a H, F, Cl, Br, I, —CN, —$CF_3$, —OH, —$OCF_3$, —$COCF_3$, —$COOCH_3$, —COOH, —N($CH_3$)$_2$, —NHBoc, —$SO_2NH_2$, —$OCH_2Ph$, or two $R^1$ groups jointly form a ring to make a naphthalene ring with the phenyl group that the $R^1$ is directly attached.

5. The compound of claim 1, wherein the compound is selected from the group consisting of:

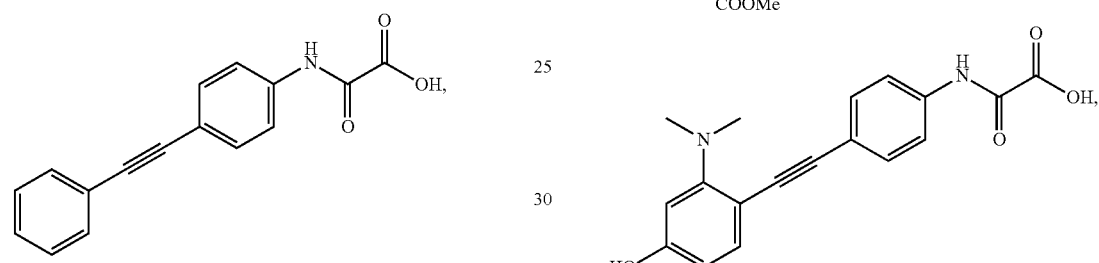

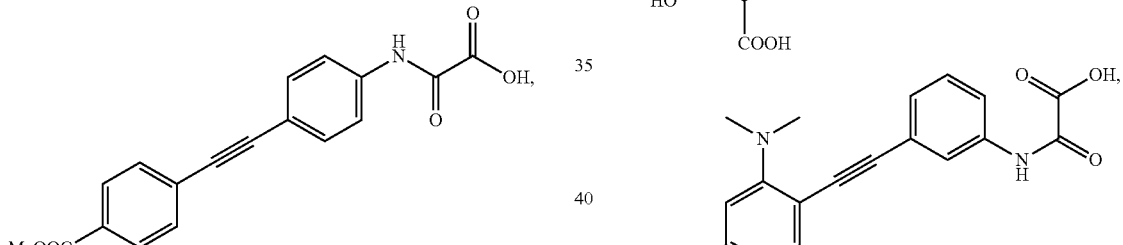

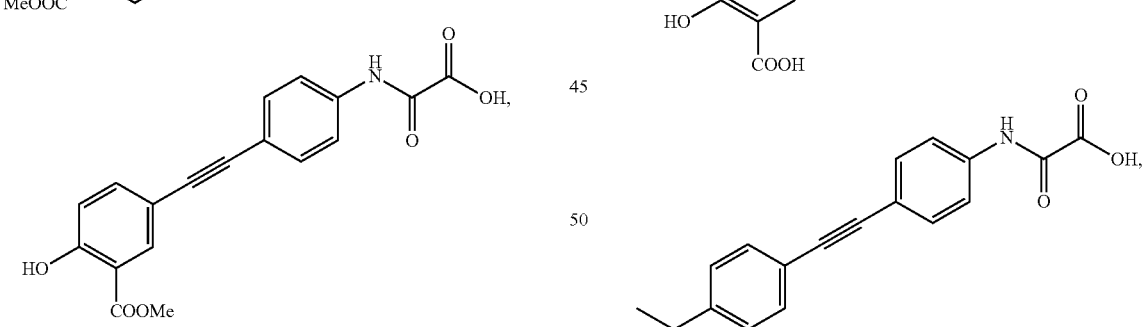

-continued

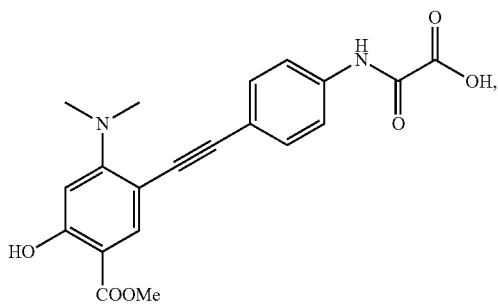

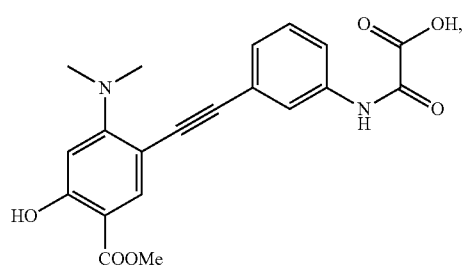

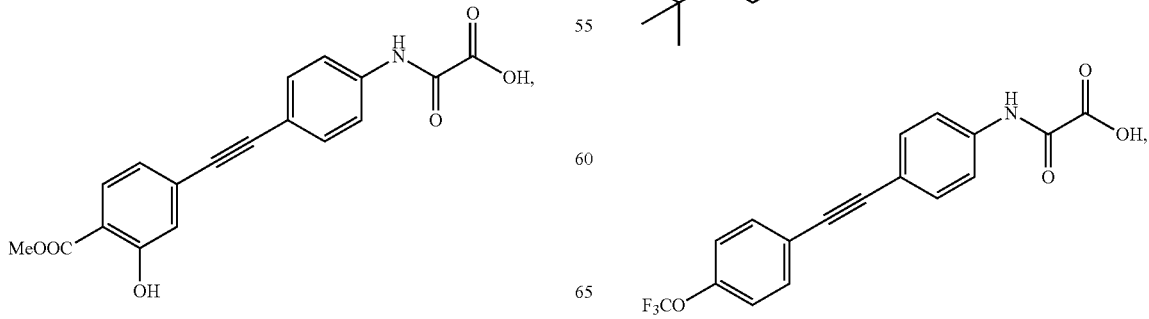

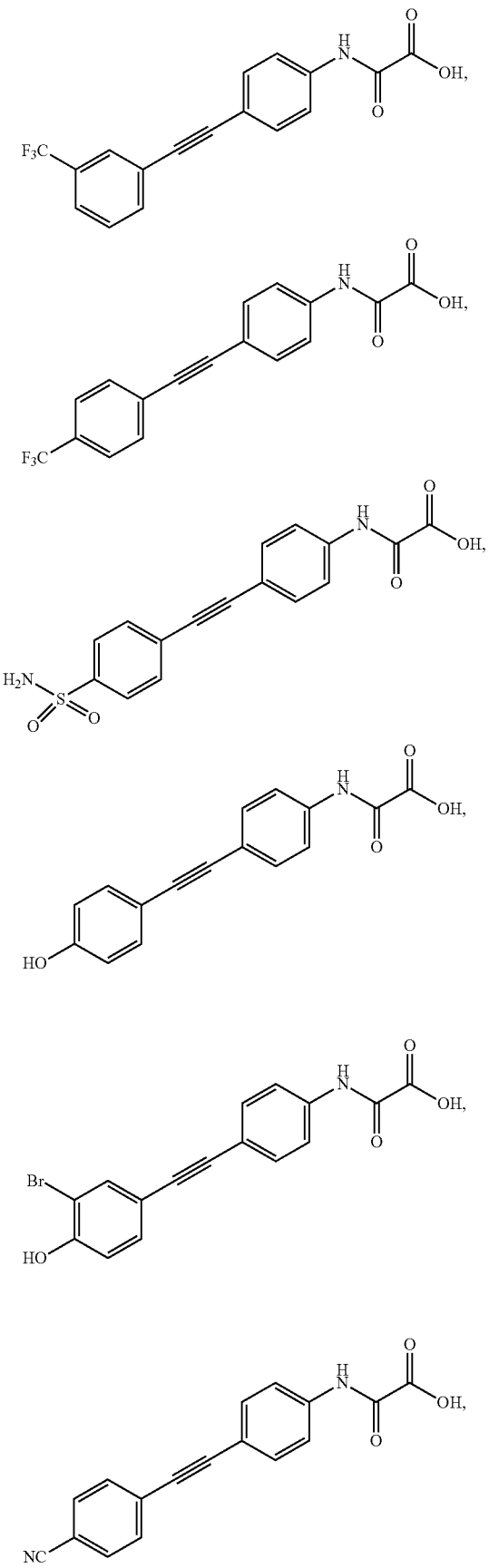
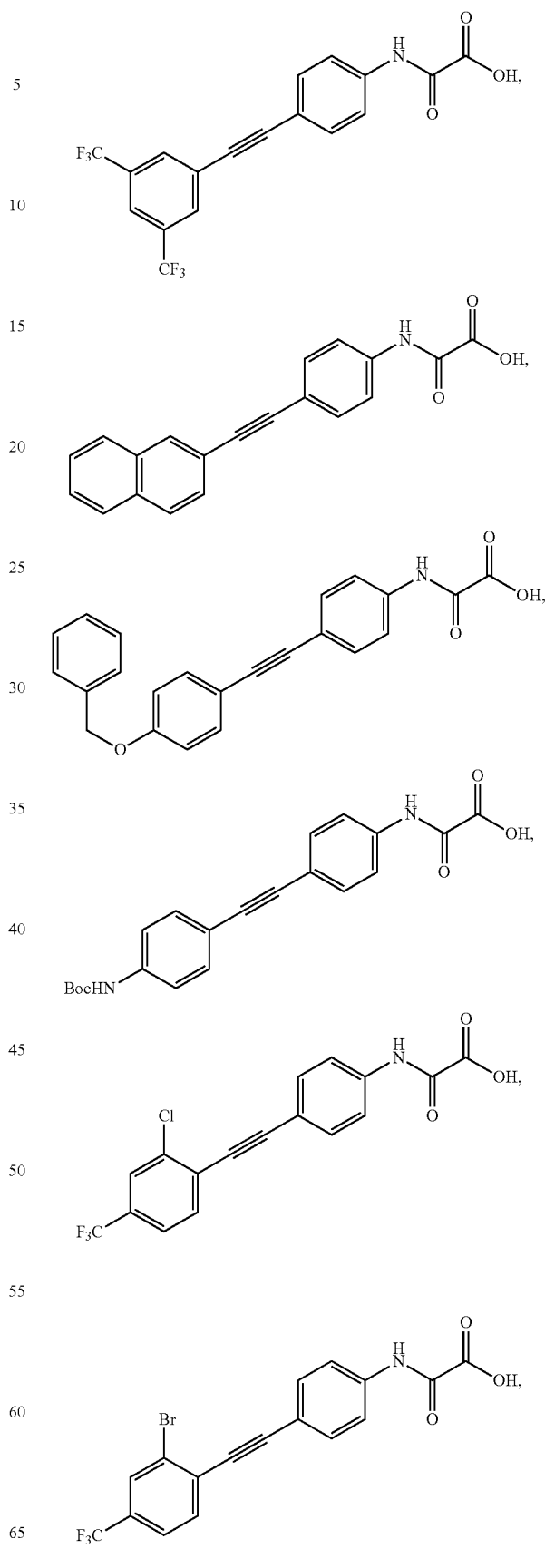

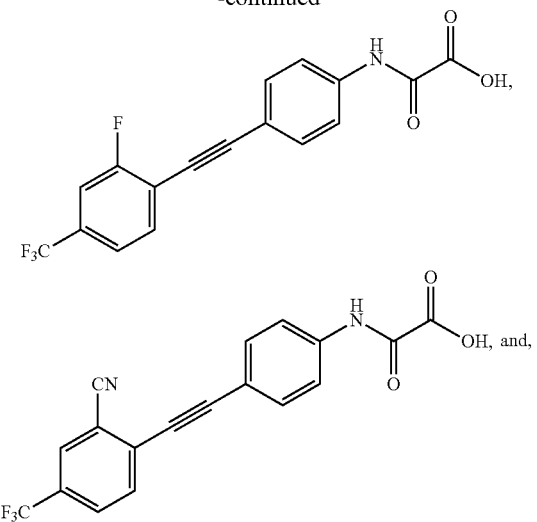

6. A method for treating a patient having a Tuberculosis disease with a compound of claim 1, or a stereoisomer, tautomer, solvate, pharmaceutically acceptable salt thereof.

7. The method of claim 6, wherein the compound of claim 1 inhibits *Mycobacterium tuberculosis* protein tyrosine phosphatase B (mPTPB).

8. The method of claim 6, wherein the compound is selected from one or more compound of claim 5.

* * * * *